(12) United States Patent
Borchardt et al.

(10) Patent No.: US 6,878,727 B2
(45) Date of Patent: Apr. 12, 2005

(54) INHIBITORS OF HEPATITIS C VIRUS RNA-DEPENDENT RNA POLYMERASE, AND COMPOSITIONS AND TREATMENTS USING THE SAME

(75) Inventors: Allen J. Borchardt, San Diego, CA (US); Michael Paul Goble, San Diego, CA (US)

(73) Assignee: Agouron Pharmaceuticals, Inc., San Diego, CA (US)

( * ) Notice: Subject to any disclaimer, the term of this patent is extended or adjusted under 35 U.S.C. 154(b) by 10 days.

(21) Appl. No.: 10/403,537

(22) Filed: Mar. 31, 2003

(65) Prior Publication Data

US 2003/0195239 A1 Oct. 16, 2003

Related U.S. Application Data

(60) Provisional application No. 60/369,381, filed on Apr. 1, 2002.

(51) Int. Cl.[7] .................. A61F 31/44; C07D 405/00
(52) U.S. Cl. ............... 514/336; 546/281.7; 548/182; 549/417
(58) Field of Search ..................... 514/460; 549/417

(56) References Cited

U.S. PATENT DOCUMENTS

| 4,591,583 A | 5/1986 | Helgstrand et al. |
| 5,846,964 A | 12/1998 | Ozeki |
| 6,169,181 B1 | 1/2001 | Romines et al. |
| 6,174,868 B1 | 1/2001 | Anderson et al. |
| 6,340,690 B1 | 1/2002 | Bachand et al. |

FOREIGN PATENT DOCUMENTS

WO          WO 02/08198         1/2002

OTHER PUBLICATIONS

Baginski, S. et. al., "Mechanism of Action of a Pestivirus Antiviral Compound," *Proc. Natl. Acad. Sci. USA,* 2000, 7981–7986, vol. 97, No. 14.

Bagshawe,K. et. al., "Antibody–Directed Enzyme Prodrug Therapy: A Review," *Drug. Development Research,* 1995, 220–230, 34.

Bartenschlager, R. et al., "Molecular Targets In Inhibition Of Hepatitis C Virus Replication" *Antiviral Chemistry & Chemotherapy* 1997, pp. 281–301, vol. 8, No. 4.

Bartenschlager, R. et al., "Nonstructural Protein 3 Of The Hepatitis C Virus Encodes A Serine–Type Proteinase Required For Cleavage At The NS3/4 And NS4/5 Junctions" *Journal of Virology,* Jul. 1993, pp. 3835–3844, vol. 67, No. 7.

Bertolini, G. et al., "A New Rational Hypothesis for the Pharmacophore of the Active Metabolite of Lefluonomide, a Potent Immunosuppressive Drug," *Journal of Med. Chem.,* 1997, 2011–2016, 40.

Bodor, N, "Novel Approaches to the Design of Safer Drugs: Soft Drugs and Site–Specific Chemical Delivery Systems," *Advances in Drug Research.,* 1984, 224–331, 13.

Brown, E. et al., "Secondary Structure Of The 5'Nontranslated Regions of Hepatitis C Virus And Pestivirus Genomic RNAs" *Nucleic Acids Research* 1992, pp. 5041–5045, vol. 20, No. 19.

Bukh, J. et al., "Sequence Analysis of the 5'Noncoding Region of Hepatitis C Virus," *Proc. National Academy of Science USA,* 1992, 4942–4946, 89.

Bungaard, H. et al. , *Design of Prodrugs,* 1985, Elsevier Press.

Choo, Q. et al., "Isolation of a cDNA Clone Derived from a Blood–Borne Non–A, Non–B Viral Hepatitis Genome," *Science,* 1989, 359–362, 244.

Cuthbert, J., "Hepatitis C: Progress and Problems" *Clinical Microbiology Reviews,* Oct. 1994, pp. 505–532, vol. 7, No. 4.

Dear, G.J. et al., "Mass Directed Peak Selection, an Efficient Method of Drug Metabolite Identification Using Directly Coupled Liquid Chromatography–Mass Spectrometry–Nuclear Magnetic Resonance Spectroscopy," *Journal of Chromatography B,* 2000, 281–293, 748.

Earl, R. et al.,, "The Preparation of 1(1H)–Pyridinones and 2,3–Dihydro–5(1H)–Indolizinones via Transition Metal Mediated Cocylization of Alkynes and Isocyanates. A Novel Construction of the Antitumor Agent Camptothecin," *Journal of Organic Chemistry,* 1984, 4786–4800, 49.

Ferrari, E. et al., "Characterization of Soluble Hepatitis C Virus RNA–Dependent RNA Polymerase Expressed in *Escherichia Coli,*" *Journal of Virology,* 1999, 1649–1654, vol. 73, No. 2.

(Continued)

*Primary Examiner*—Kamal Saeed
(74) *Attorney, Agent, or Firm*—Peter C. Richardson; Bryan C. Zielinski; Keith D. Hutchinson

(57) ABSTRACT

Compounds of formula I are hepatitis C virus (HCV) RNA-dependent RNA polymerase (RdRp) inhibitors, and are useful in therapeutic and prophylactic treatment of persons infected with hepatitis C virus

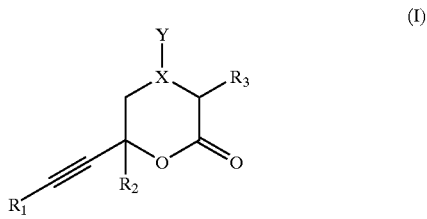

(I)

9 Claims, No Drawings

OTHER PUBLICATIONS

Friis, G. et al., *Design and Application of Prodrugs, Drug Design and Development,* 1991, Harwood Academic Publishers.

Grakoui, A. et al., "Expression And Identification Of Hepatitis C Virus Polyprotein Cleavage Products" *Journal Of Virology,* Mar. 1993, pp. 1385–1395, vol. 67, No. 3.

Hajimorad, et al., "Some Observations On The Binding Properties Of Alfalfa Mosaic Virus To Polystyrene And It's Significance To Indirect ELISA" Arch Virol., 1991, pp. 219–235, vol. 117.

Hijikata, M. et al., "Gene Mapping of the Putative Structural Region of the Hepatitis C Virus Genome by In Vitro Processing Analysis," *Proc. Natl. Acad. Science USA,* 1991, 5547–5551, 88.

Hwang, S. et al., "Hepatitis C Virus NS5B Protien Is A Membrane–Associated Phosphoprotein With A Predominantly Perinuclear Localization," *Virology,* 1997, pp. 439–446, vol. 227.

Ishii, K. et. al., "Expression of Hepatitis C Virus NS5B Protein: Characterization of Its RNA Polymerase Activity and RNA Binding," *Hepatology,* 1999, 1227–1235, vol. 29, No. 4.

Jamison, D. et al., *World Health Organization,* 1998, 514–517, 351.

Kim, J. et. al., "Crystal Structure of the Hepatitis C Virus NS3 Protease Domain Complexed with a Synthetic NS4A Cofactor Peptide," *Cell,* 1996, 343–355, 87.

Kim., J. et. al., "Hepatitis C Virus NS3 RNA Helicase Domain with a Bound Oligonucleotide: The Crystal Structure Provides Insights into the Mode of Unwinding," *Structure,* 1998, 89–100, 6.

Kolykhalov, et. al., "Identification of a Highly Conserved Sequence Element at the 3' Terminus of Hepatitis C Virus Genome RNA," *Journal of Virology,* 1996, 3363–3371, vol. 70, No. 9.

Kunz, K., "A Simple and Convenient Synthesis of 5–Substituted Benzoxazoles," *Organic Preparations and Procedures, Int.,* 1990, 613–618, vol. 22, No. 5.

Lin, et al., "Processing in the Hepatitis C Virus E2–NS2 Region: Identification of p7 and Two Distinct E2–Specific Products with Different C Termini," Journal of Virology, 1994, 5063–5073, vol. 68, No. 8.

Lohmann, V. et. al., "Biochemical and Kinetics Analyses of NS5B RNA–Dependent RNA Polymerase of the Hepatitis C Virus," *Virology,* 1998, 108–118, 249.

Lohmann, V. et. al., "Biochemical Properties of Hepatitis C Virus NS5B RNA–Dependent RNA Polymerase and Identification of Amino Acid Sequence Motifs Essential for Enzymatic Activity," *Journal of Virology,* 1997, 8416–8428, vol. 71, No. 11.

Love, R. et. al., "The Crystal Structure of Hepatitis C Virus NS3 Proteinase Reveals a Trypsin–like Fold and a Structural Zinc Binding Site.," *Cell,* 1996, 331–342, 87.

Marcellin, P. et. al., "Long–Term Histologic Improvement and Loss of Detectable Intrahepatic HCV RNA in Patients with Chronic Hepatitis C and Sustained Response to Interferon–alpha Therapy," *Annals of Internal Medicine,* 1997, 875–881, 127.

May, Q. et al., "Recent Advances In Prevention And Treatment Of Hepatitis C Virus Infections," *Process in Drug Research,* 2000, pp. 1–32, 55.

McKillop, A. et. al., "Reaction of Benzothiazole and Substituted Benzothiazoles with Dimethyl Acetylenedicarboxylate. A Novel Heterocyclic Ring Transformation," *Journal of Organic Chemistry,* 1876, 1328–1331, vol. 41 No. 8.

Miller, R. et. al., "Hepatitis C Virus Shares Amino Acid Sequence Similarity with Pestiviruses and Flaviviruses as well as Members of Two Plant Virus Supergroups," *Proc. Natl. Academy of Science USA,* 1990, 2057–2061, 87.

Poch, O. et al., "Identification Of Four Conserved Motifs Among The RNA–Dependent Polymerase Encoding Elements" *The EMBO Journal,* 1989, pp. 3867–3874, vol. 8, No. 12.

Prox, et. al., "Rapid Structure Elucidation of Drug Metabolites by Use of Stable Isotopes," *Xenobiotica,* 1973, 103–112, vol. 3 No. 2.

Rink, Hans, "Solid–Phase Synthesis Of Protected Peptide Fragments Using A Trialkoxy–Diphenyl–Methylester Resin." Tetrahedron Letters, 1987, pp. 3787–3790, vol. 28, No. 33.

Shan, D. et. al., "Prodrug Strategies Based on Intramolecular Cyclization Reactions," *Journal of Pharmaceutical Sciences,* 1997, 765–767, vol. 86, No. 7.

Simmonds, P. et. al., Classification Of Hepatitis C Virus Into Six Journal of Gen. Virology, 1993, 2391–2399, 74.

Spraul, M. et. al., "Liquid Chromatography Coupled With High–Field Proton NMR For Profiling Human Urine For Endogenous Compounds and Drug Metabolites" *Journal of Pharmaceutical & Biomedical Analysis,* 1992, 601–605, vol. 10 No. 8.

Tanaka, T. et. al., "Structure of the 3' Terminus of the Hepatitis C Virus Genome," *Journal of Virology,* 1996, 3307–3312, vol. 70, No. 5.

Weiner, A. et al., "Evidence For Immune Selection Of Hepatitis C Virus (HCV) Putative Envelope Glycoprotein Variants: Potential Role In Chronic HCV Infections," *Proc. Natl. Acad. Sci. USA,* Apr. 1992, pp. 3468–3472, vol. 89.

Weiner, A. et al., "Variable And Hypervariable Domains Are Found In The Regiosn Of HCV Corresponding To The Flavivirus Envelope And NS1 Proteins And The Pestivirus Envelope Glycoproteins" *Virology,* 1991, pp. 842–848, vol. 180.

Wyatt, C. et. al., "Immunity in Chimpanzees Chronically Infected with Hepatitis C Virus: Role of Minor Quasispecies in Reinfection," *Journal of Virology,* 1998, 1725–1730, vol. 72, No. 3.

Yamashita, T. et. al., "RNA–dependent RNA Polymerase Activity of the Soluble Recombinant Hepatitis C Virus NS5B Protein Truncated at the C–terminal Region," *Journal of Biol. Chem.,* 1998, 15479–15486, 273.

Zeuzem, S. et. al., "Hepatitis C Virus Dynamics in Vivo: Effect of Ribavirin and Interferon Alfa on Viral Turnover," *Hepatology,* 1998, 245–252, 28.

Okamoto, T. et al. "Reaction of N–Aminopyridinium Derivatives. M. Properties of s–Triazolo[1,5–α]pyridine Ring." *Chem. Pharm. Bull.* (1996) 523–528, vol. 14, No. 5.

INHIBITORS OF HEPATITIS C VIRUS RNA-DEPENDENT RNA POLYMERASE, AND COMPOSITIONS AND TREATMENTS USING THE SAME

This application claims the benefit of U.S. Provisional Application Ser. No. 60/369,381, filed Apr. 1, 2002.

FIELD OF THE INVENTION

The invention relates to agents that inhibit hepatitis C virus (HCV) RNA-dependent RNA polymerase (RdRp). The invention also relates to the use of such compounds in pharmaceutical compositions and therapeutic treatments useful for inhibition of HCV replication.

BACKGROUND OF THE INVENTION

Hepatitis C virus (HCV) is a member of the hepacivirus genus in the family *Flaviviridae*. It is the major causative agent of non-A, non-B viral hepatitis and is the major cause of transfusion-associated hepatitis and accounts for a significant proportion of hepatitis cases worldwide. Although acute HCV infection is often asymptomatic, nearly 80% of cases resolve to chronic hepatitis. The persistent property of the HCV infection has been explained by its ability to escape from the host immune surveillance through hypermutability of the exposed regions in the envelope protein E2 (Weiner et al., *Virology* 180:842–848 (1991); Weiner et al. *Proc. Natl. Acad. Sci. USA* 89:3468–3472 (1992). About 60% of patients develop liver disease with various clinical outcomes ranging from an asymptomatic carrier state to chronic active hepatitis and liver cirrhosis (occurring in about 20% of patients), which is strongly associated with the development of hepatocellular carcinoma (occurring in about 1–5% of patients) (for reviews, see Cuthbert, *Clin. Microbiol. Rev.* 7:505–532 (1994); World Health Organization, *Lancet* 351:1415 (1998). The World Health Organization estimates that 170 million people are chronically infected with HCV, with an estimate of 4 million of these living in the United States.

HCV is an enveloped RNA virus containing a single-stranded positive-sense RNA genome approximately 9.5 kb in length (Choo et al., *Science* 244:359–362 (1989)). The RNA genome contains a 5'-nontranslated region (5' NTR) of 341 nucleotides (Brown et al., *Nucl. Acids Res.* 20:5041–5045 (1992); Bukh et al., *Proc. Natl. Acad. Sci. USA* 89:4942–4946 (1992)), a large open reading frame (ORF) encoding a single polypeptide of 3,010 to 3,040 amino acids (Choo et al. (1989), supra;), and a 3'-nontranslated region (3'-NTR) of variable length of about 230 nucleotides (Kolykhalov et al., *J. Virol.* 70:3363–3371 (1996); Tanaka et al., *J. Virol.* 70:3307–3312 (1996)). By analogy to other plus-strand RNA viruses, the 3' nontranslated region is assumed to play an important role in viral RNA synthesis. HCV is similar in amino acid sequence and genome organization to flaviviruses and pestiviruses (Miller et al., *Proc. Natl. Acad. Sci. USA* 87:2057–2061 (1990)), and therefore HCV has been classified as a third genus of the family *Flaviviridae* (Francki et al., *Arch. Virol.* 2:223–233 (1991).

Studies of HCV replication and the search for specific anti-HCV agents have been hampered by the lack of an efficient tissue culture system for HCV propagation, the absence of a suitable small-animal model for HCV infection, the low level of viral replication, and the considerable genetic heterogeneity associated with the virus (Bartenschlager, *Antivir. Chem. Chemother.* 8:281–301 (1997); Simmonds et al., *J. Gen. Virol.* 74:2391–2399 (1993)). The current understanding of the structures and functions of the HCV genome and encoded proteins is primarily derived from in vitro studies using various recombinant systems (Bartenschlager (1997), supra).

The 5' NTR is one of the most conserved regions of the viral genome and plays a pivotal role in the initiation of translation of the viral polyprotein (Bartenschlager (1997), supra). A single long ORF encodes a polyprotein, which is co- or post-translationally processed into structural (core, E1, and E2) and nonstructural (NS2, NS3, NS4A, NS4B, NS5A, and NS5B) viral proteins by either cellular or viral proteinases (Bartenschlager (1997), supra). The 3' NTR consists of three distinct regions: a variable region of about 38 nucleotides following the stop codon of the polyprotein, a polyuridine tract of variable length with interspersed substitutions of cytidines, and 98 nucleotides (nt) at the very 3' end which are highly conserved among various HCV isolates. The order of the genes within the genome is: $NH_2$—C-E1-E2-p7-NS2-NS3-NS4A-NS4B-NS5A-NS5B-COOH (Grakoui et al., *J. Virol.* 67:1385–1395 (1993)).

Processing of the structural proteins core (C), envelope protein 1 and (E1, E2), and the p7 region is mediated by host signal peptidases. In contrast, maturation of the nonstructural (NS) region is accomplished by two viral enzymes. The HCV polyprotein is first cleaved by a host signal peptidase generating the structural proteins C/E1, E1/E2, E2/p7, and p7/NS2 (Hijikata et al., *Proc. Natl. Acad. Sci. USA* 88:5547–5551 (1991); Lin et al., *J. Virol.* 68:5063–5073 (1994)). The NS2–3 proteinase, which is a metalloprotease, then cleaves at the NS2/NS3 junction. The NS3/4A proteinase complex (NS3 being a serine protease and NS4A acting as a cofactor of the NS3 protease), is then responsible for processing at all the remaining sites (Bartenschlager et al.,*J. Virol.* 67:3835–3844 (1993); Bartenschlager (1997), supra). RNA helicase and NTPase activities have also been identified in the NS3 protein. The N-terminal one-third of the NS3 protein functions as a protease, and the remaining two-thirds of the molecule acts as the helicase/ATPase that is thought to be involved in HCV replication (Bartenschlager (1997), supra). NS5A may be phosphorylated and act as a putative cofactor of NS5B. The fourth viral enzyme, NS5B, is an RNA-dependent RNA polymerase (RdRp) and a key component responsible for replication of the viral RNA genome (Lohmann et al., *J. Virol.* 71:8416–8428 (1997)). NS5B contains the "GDD" sequence motif, which is highly conserved among all RdRps characterized to date (Poch et al., *EMBO J.* 8:3867–3874 (1989)).

Replication of HCV is thought to occur in membrane-associated replication complexes. Within these, the genomic plus-strand RNA is transcribed into minus-strand RNA, which in turn can be used as a template for synthesis of progeny genomic plus strands. At least two viral proteins appear to be involved in this reaction: the NS3 protein, which carries in the carboxy terminal two-thirds a nucleoside triphosphatase/RNA helicase, and the NS5B protein, which is a membrane-associated phosphoprotein with an RNA-dependent RNA polymerase activity (RdRp) (Hwang et al., *J. Virol.* 227:439–446 (1997)). While the role of NS3 in RNA replication is less clear, NS5B apparently is the key enxyme responsible for synthesis of progeny RNA strands. Using recombinant baculoviruses to express NS5B in insect cells and a synthetic nonviral RNA as a substrate, two enzymatic activities have been identified as being associated with it: a primer-dependent RdRp and a terminal transferase (TNTase) activity. It was subsequently confirmed and further characterized through the use of the HCV RNA genome as a substrate (Lohmann et al., *Virology* 249:108–118 (1998)). Recent studies have shown that NS5B with a C-terminal 21 amino-acid truncation expressed in *Escherichia coli* is also active for in vitro RNA synthesis (Ferrari et al., *J. Virol.* 73:1649–1654 (1999); Yamashita et al., *J. Biol. Chem.* 273:15479–15486 (1998)).

Since persistent infection of HCV is related to chronic hepatitis and eventually to hepatocarcinogenesis, HCV replication is one of the targets to eradicate HCV reproduction and to prevent hepatocellular carcinoma. Unfortunately, present treatment approaches for HCV infection are characterized by relatively poor efficacy and an unfavorable side-effect profile. Therefore, intensive effort is directed at the discovery of molecules to treat this disease. These new approaches include the development of prophylactic and therapeutic vaccines, the identification of interferons with improved pharmacokinetic characteristics, and the discovery of drugs designed to inhibit the function of three major viral proteins: protease, helicase and polymerase. Also, the HCV RNA genome itself, particularly the IRES element, is being actively exploited as an antiviral target using antisense molecules and catalytic ribozymes. For a review, see Wang et al., *Prog. Drug Res.* 55:1–32 (2000).

Particular therapies for HCV infection include α-interferon alone and the combination of α-interferon with ribavirin. These therapies have been shown to be effective in a portion of patients with chronic HCV infection (Marcellin et al., *Ann. Intern. Med.* 127:875–881 (1997); Zeuzem et al., *Hepatology* 28:245–252 (1998)). Use of antisense oligonucleotides for treatment of HCV infection has also been proposed (Anderson et al., U.S. Pat. No. 6,174,868 (2001)) as well as use of free bile acids, such as ursodeoxycholic acid and chenodeoxycholic acid, or conjugated bile acids, such as tauroursodeoxycholic acid (Ozeki, U.S. Pat. No. 5,846,964 (1998)). Phosphonoformic acid esters have also been proposed to be useful in treating a number of viral infections including HCV (Helgstrand et al., U.S. Pat. No. 4,591,583 (1986)). Vaccine development has been hampered by the high degree of immune evasion and the lack of protection against reinfection, even with the same inoculum (Wyatt et al., *J. Virol.* 72:1725–1730 (1998)).

The development of small-molecule inhibitors directed against specific viral targets has become a focus of anti-HCV research. The determination of crystal structures for NS3 protease (Kim et al., *Cell* 87:343–355 (1996); Love et al., *Cell* 87:331–342 (1996)) and NS3 RNA helicase (Kim et al. *Structure* 6:89–100 (1998)) has provided important structural insights for rational design of specific inhibitors.

NS5B, the RNA-dependent RNA polymerase, is also a useful viral target for small-molecule inhibitors. Studies with pestiviruses have shown that the small compound VP32947 (3-[((2-dipropylamino)ethyl)thio]-5H-1,2,4-triazino[5,6-b]indole) is a potent inhibitor of pestivirus replication and most likely inhibits the NS5B enzyme since resistant strains are mutated in this gene (Baginski et al., *Proc. Natl. Acad. Sci. USA* 97:7981–7986 (2000)). Inhibition of RdRp activity by (-)β-L-2',3'-dideoxy-3'-thiacytidine 5'-triphosphate (3TC; lamivudine triphosphate) and phosphonoacetic acid also has been observed (Ishii et al., *Hepatology* 29:1227–1235 (1999)).

Nonetheless, there is still a need for non-peptide, small-molecule compounds that are HCV RdRp inhibitors and that have desirable or improved physical and chemical properties appropriate for pharmaceutical applications.

SUMMARY OF THE INVENTION

The present invention is directed to compounds that function as inhibitors to hepatitis C virus RNA-dependent RNA polymerase. The invention is also directed to the use of such compounds in pharmaceutical compositions and therapeutic treatments useful for inhibition of HCV replication.

In one general aspect, the invention is directed to compounds represented by formula I:

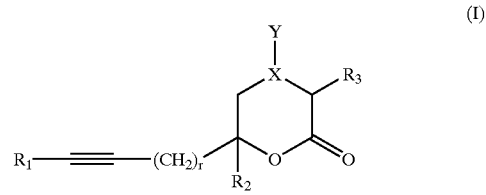

wherein:

r is 0, 1, 2, 3, 4 or 5;

Y is =O or —O(CH$_m$)$_n$, where m is 2 or 3 and n is an integer from 0 to 5;

X is

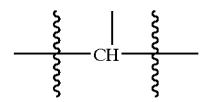

when Y is —O(CH$_m$)$_n$ and X is

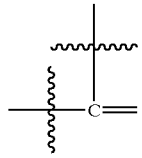

when Y is =O; or X and Y taken together form

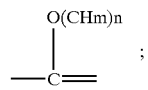

R$_1$ is hydrogen, or an aryl, heteroaryl, or heterocycloalkyl group unsubstituted or substituted with one or more substituents selected from the group consisting of halogens; =O; =S; —CN; —NO$_2$; alkyl; heteroalkyl; alkenyl; alkynyl; aryl; cycloalkyl; heterocycloalkyl; heteroaryl; alkoxy; —(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHNH; —NHS(O)H; —NHSO$_2$H; —C(O)SH; —C(O)S(O)H; —C(O)S(O$_2$)H; —C(S)OH; —C(SO)OH; —C(SO$_2$)OH; —NHC(S)H; —OC(S)H; —OC(S)OH; —OC(SO$_2$)H; —S(O$_2$)NH$_2$; —S(O)NH$_2$; —SNH$_2$; —NHCS(O$_2$)H; —NHC(SO)H; —NHC(S)H; and —SH groups, unsubstituted or substituted with one or more substituents selected from the group consisting of halogens; =O; =S; —CN; —NO$_2$; alkyl; heteroalkyl; alkenyl; alkynyl; aryl; cycloalkyl; heterocycloalkyl; heteroaryl; alkoxy;

—(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHSH; —NHS(O)H; —NHSO$_2$H; —C(O)SH; —C(O)S(O)H; —C(O)S(O$_2$)H; —C(S)H; —C(SO)OH; —C(SO$_2$)OH; —NHC(S)H; —OC(S)H; —OC(S)OH; —OC(SO$_2$)H; —S(O$_2$)NH$_2$; —S(O)NH$_2$; —SNH$_2$; —NHCS(O$_2$)H; —NHC(SO)H; —NHC(S)H; and —SH groups; and R$_2$ is a cyclopentyl group, unsubstituted or substituted with one or more substituents selected from the group consisting of halogens; =O; =S; —CN; —NO$_2$; alkyl; alkenyl; alkynyl; aryl; cycloalkyl; heterocycloalkyl; heteroaryl; —(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHSH; —NHS(O)H; —NHSO$_2$H; —C(O)SH; —C(O)S(O)H; —C(O)S(O$_2$)H; —C(S)OH; —C(SO)OH; —C(SO$_2$)OH; —NHC(S)H; —OC(S)H; —OC(S)OH; —OC(SO$_2$)H; —S(O$_2$)NH$_2$; —S(O)NH$_2$; —SNH$_2$; —NHCS(O$_2$)H; —NHC(SO)H; —NHC(S)H; and —SH groups; and R$_3$ is hydrogen, =S, or SH unsubstituted or substituted with an aryl group.

The invention is also directed to pharmaceutically acceptable salts and active metabolites of compounds of formula I. Such compounds, salts and active metabolites are sometimes referred to herein as "HCV-inhibiting agents."

The invention is futher directed to pharmaceutical compositions each comprising an effective HCV-inhibiting amount of a compound of formula I, or a pharmaceutically acceptable salt or active metabolite thereof together with a pharmaceutically acceptable carrier therefor.

The invention also provides methods of inhibiting HCV polymerase activity comprising contacting an HCV polymerase with an effective amount of a compound, salt or active metabolite of formula I.

The invention further provides methods of inhibiting HCV polymerase activity in mammalian tissue or human tissue by administering an effective amount of a compound, salt or active metabolite of formula I to a mammal or a human.

The invention is yet further directed to methods of inhibiting HCV polymerase activity wherein the compound, salt or active metabolite of formula I is administered to a human orally or intravenously.

Other features and advantages of the invention will be apparent from the description that follows, which illustrates the invention and its preferred embodiments.

DETAILED DESCRIPTION OF THE INVENTION AND PREFERRED EMBODIMENTS

HCV-Inhibiting Agents

As used herein, the terms "comprising" and "including" are used in their open, non-limiting sense.

In accordance with a convention used in the art, the symbol

is used in structural formulas herein to depict the bond that is the point of attachment of the moiety or substituent to the core or backbone structure. In accordance with another convention, in some structural formulae herein the carbon atoms and their bound hydrogen atoms are not explicitly depicted, e.g.,

represents a methyl group,

represents an ethyl group,

represents a cyclopentyl group, etc.

As used herein, the term "alkyl" means a branched- or straight-chained (linear) paraffinic hydrocarbon group (saturated aliphatic group) having from 1 to 12 carbon atoms in its chain, which may be generally represented by the formula $C_kH_{2k+1}$, where k is an integer of from 1 to 10. Examples of alkyl groups include methyl, ethyl, n-propyl, isopropyl, n-butyl, isobutyl, t-butyl, pentyl, n-pentyl, isopentyl, neopentyl, hexyl, and the like. A "lower alkyl" is intended to mean an alkyl group having from 1 to 4 carbon atoms in its chain. The term "heteroalkyl" refers to a straight- or branched-chain alkyl group having from 2 to 12 atoms in the chain, one or more of which is a heteroatom selected from S, O, and N. Exemplary heteroalkyls include alkyl ethers, secondary and tertiary amines, alkyl sulfides and the like.

The term "alkenyl" means a branched- or straight-chained olefinic hydrocarbon group (unsaturated aliphatic group having one or more double bonds) containing 2 to 12 carbons in its chain. Exemplary alkenyls include ethenyl, 1-propenyl, 2-propenyl, 1-butenyl, 2-butenyl, isobutenyl, and the like.

The term "alkynyl" means a branched or straight-chained hydrocarbon group having one or more carbon-carbon triple bonds, and having from 2 to 12 carbon atoms in its chain. Exemplary alkenyls include ethenyl, propynyl, 1-butynyl, 2-butynyl, 2-pentynyl, 2-methylbur-2-ynyl, and the like.

The term "carbocycle" refers to a saturated, partially saturated, unsaturated, or aromatic, monocyclic or fused or non-fused polycyclic, ring structure having only carbon ring atoms (no heteroatoms, i.e., non-carbon ring atoms). Exemplary carbocycles include cycloalkyl, aryl, and cycloalkyl-aryl groups.

The term "heterocycle" refers to a saturated, partially saturated, unsaturated, or aromatic, monocyclic or fused or non-fused polycyclic, ring structure having one or more heteroatoms selected from N, O, and S. Exemplary heterocycles include heterocycloalkyl, heteroaryl, and heterocycloalkyl-heteroaryl groups.

A "cycloalkyl group" is intended to mean a saturated or partially saturated, monocyclic, or fused or spiro polycyclic, ring structure having a total of from 3 to 18 carbon ring atoms (but no heteroatoms). Exemplary cycloalkyls include cyclopropyl, cyclobutyl, cyclopentyl, cyclopentenyl, cyclohexyl, cycloheptyl, adamantyl, and like groups.

A "heterocycloalkyl group" is intended to mean a monocyclic, or fused or spiro polycyclic, ring structure that is saturated or partially saturated, and has a total of from 3 to 18 ring atoms, including 1 to 5 heteroatoms selected from nitrogen, oxygen, and sulfur. Illustrative examples of heterocycloalkyl groups include pyrrolidinyl, tetrahydrofuryl, piperidinyl, piperazinyl, morpholinyl, thiomorpholinyl, aziridinyl, and like groups.

The term "aryl" means an aromatic monocyclic or fused or spiro polycyclic ring structure having a total of from 4 to 18 ring carbon atoms (no heteroatoms). Exemplary aryl groups include phenyl, naphthyl, anthracenyl, and the like.

A "heteroaryl group" is intended to mean a monocyclic or fused or spiro polycyclic, aromatic ring structure having from 4 to 18 ring atoms, including from 1 to 5 heteroatoms selected from nitrogen, oxygen, and sulfur. Illustrative examples of heteroaryl groups include pyrrolyl, thienyl, oxazolyl, pyrazolyl, thiazolyl, furyl, pyridinyl, pyrazinyl, triazolyl, tetrazolyl, indolyl, quinolinyl, quinoxalinyl, benzthiazolyl, benzodioxinyl, benzodioxolyl, benzooxazolyl, and the like.

The term "alkoxy" is intended to mean the radical —OR$_a$, where R$_a$ is an alkyl group. Exemplary alkoxy groups include methoxy, ethoxy, propoxy, and the like. "Lower alkoxy" groups have alkyl moieties having from 1 to 4 carbons.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents.

A "HCV-inhibiting agent" means a compound represented by formula I or a pharmaceutically acceptable salt, prodrug, active metabolite or solvate thereof.

A "prodrug" is a compound that may be converted under physiological conditions or by solvolysis to the specified compound or to a pharmaceutically acceptable salt of such compound. An "active metabolite" is a pharmacologically active product produced through metabolism in the body of a specified compound or salt thereof. Prodrugs and active metabolites of a compound may be identified using routine techniques known in the art. See, e.g., Bertolini et al., *J. Med. Chem.*, (1997) 40:2011–2016; Shan et al., *J. Pharm. Sci.*, 86 (7):765–767; Bagshawe, *Drug Dev. Res.,* (1995) 34:220–230; Bodor, *Advances in Drug Res.*, (1984) 13:224–331; Bundgaard, *Design of Prodrugs* (Elsevier Press 1985); Larsen, *Design and Application of Prodrugs*, Drug Design and Development (Krogsgaard-Larsen et al. eds., Harwood Academic Publishers, 1991); Dear et al., *J. Chromatogr. B*, (2000) 748:281–293; Spraul et al., *J. Pharmaceutical & Biomedical Analysis*, (1992) 10 (8):601–605; and Prox et al., *Xenobiol*, (1992) 3(2):103–112.

A "solvate" is intended to mean a pharmaceutically acceptable solvate form of a specified compound that retains the biological effectiveness of such compound. Examples of solvates include compounds of the invention in combination with water, isopropanol, ethanol, methanol, DMSO, ethyl acetate, acetic acid, or ethanolamine. A "pharmaceutically acceptable salt" is intended to mean a salt that retains the biological effectiveness of the free acids and bases of the specified compound and that is not biologically or otherwise undesirable. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycollates, tartrates, methanesulfonates, propanesulfonates, naphthalene-1-sulfonates, naphthalene-2-sulfonates, and mandelates.

If an inventive compound is a base, a desired salt may be prepared by any suitable method known to the art, including treatment of the free base with an inorganic acid, such as hydrochloric acid; hydrobromic acid; sulfuric acid; nitric acid; phosphoric acid; and the like, or with an organic acid, such as acetic acid; maleic acid; succinic acid; mandelic acid; fumaric acid; malonic acid; pyruvic acid; oxalic acid; glycolic acid; salicylic acid; pyranosidyl acid, such as glucuronic acid or galacturonic acid; alpha-hydroxy acid, such as citric acid or tartaric acid; amino acid, such as aspartic acid or glutamic acid; aromatic acid, such as benzoic acid or cinnamic acid; sulfonic acid, such as p-toluenesulfonic acid or ethanesulfonic acid; and the like.

If an inventive compound is an acid, a desired salt may be prepared by any suitable method known to the art, including treatment of the free acid with an inorganic or organic base, such as an amine (primary, secondary, or tertiary); an alkali metal or alkaline earth metal hydroxide; or the like. Illustrative examples of suitable salts include organic salts derived from amino acids such as glycine and arginine; ammonia; primary, secondary, and tertiary amines; and cyclic amines, such as piperidine, morpholine, and piperazine; as well as inorganic salts derived from sodium, calcium, potassium, magnesium, manganese, iron, copper, zinc, aluminum, and lithium.

In the case of compounds, salts, or solvates that are solids, it is understood by those skilled in the art that the inventive compounds, salts, and solvates may exist in different polymorph or crystal forms, all of which are intended to be within the scope of the present invention and specified formulas.

In some cases, the inventive compounds will have chiral centers. When chiral centers are present, the inventive compounds may exist as single stereoisomers, racemates, and/or mixtures of enantiomers and/or diastereomers. All such single stereoisomers, racemates, and mixtures thereof are intended to be within the broad scope of the present invention.

As generally understood by those skilled in the art, an optically pure compound is one that is enantiomerically pure. As used herein, the term "optically pure" is intended to mean a compound comprising at least a sufficient activity. Preferably, an optically pure amount of a single enantiomer to yield a compound having the desired pharmacological pure compound of the invention comprises at least 90% of a single isomer (80% enantiomeric excess), more preferably at least 95% (90% e.e.), even more preferably at least 97.5% (95% e.e.), and most preferably at least 99% (98% e.e.).

Exemplary compounds of the invention represented by formula I include:

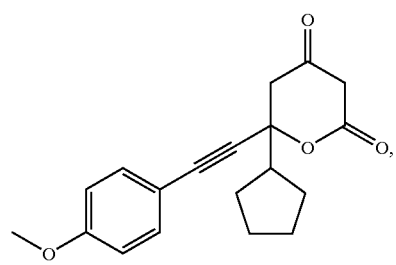
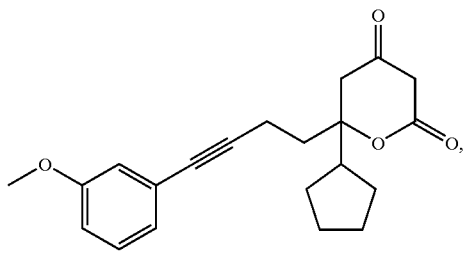
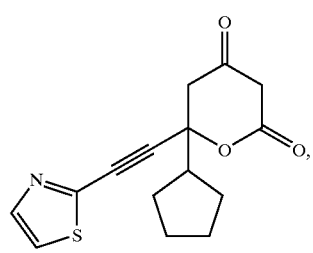
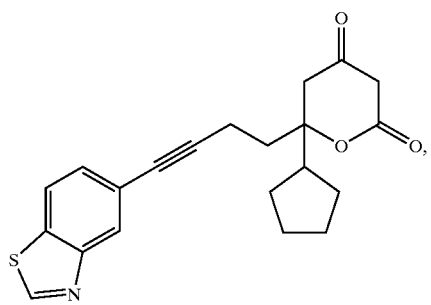
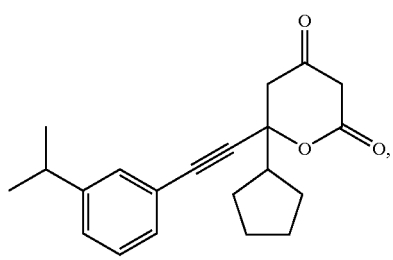
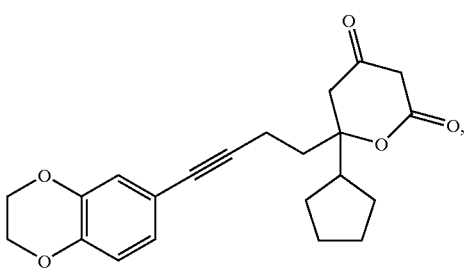
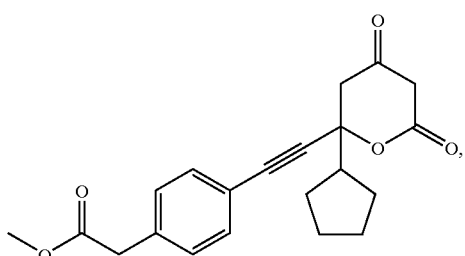
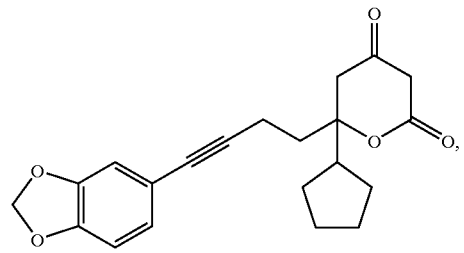
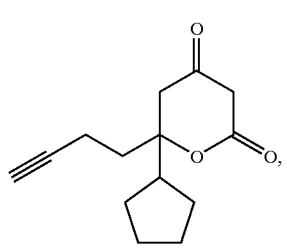
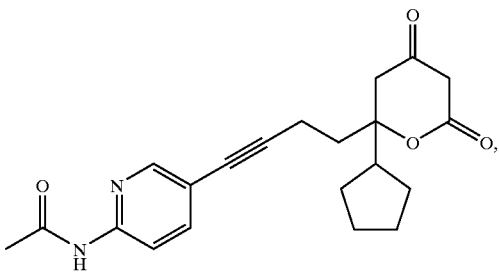
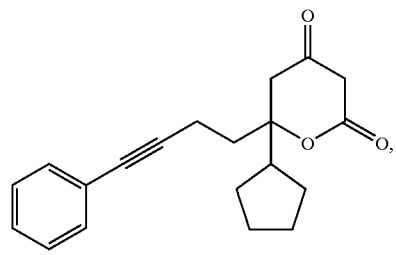
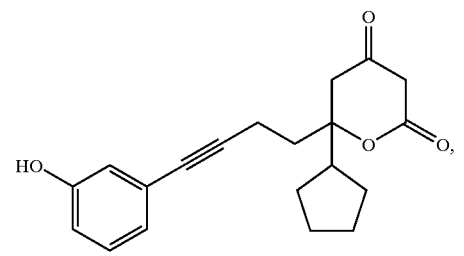

-continued
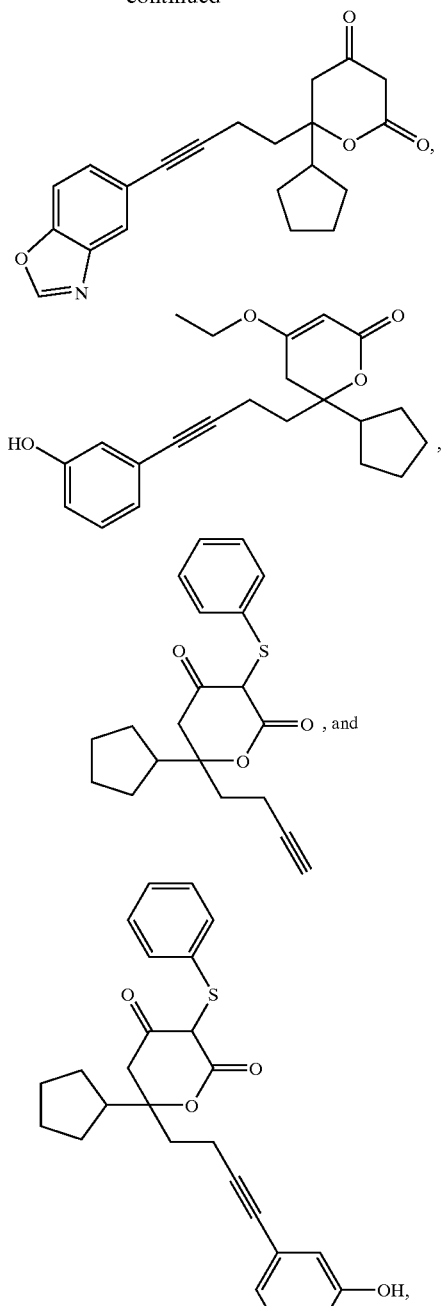
and pharmaceutically acceptable salts, prodrugs, active metabolites, and solvates thereof.
Preferred compounds of the invention of formula I include:
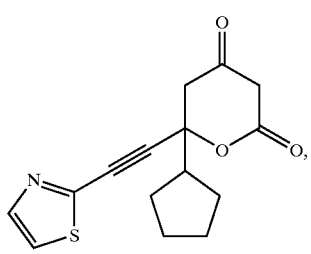
-continued
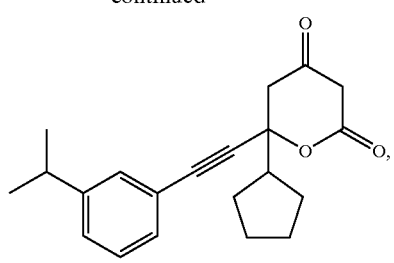
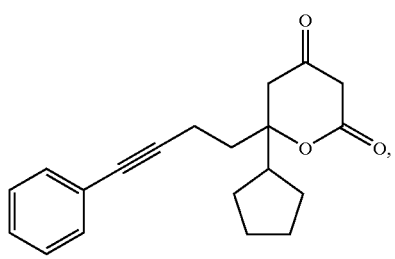
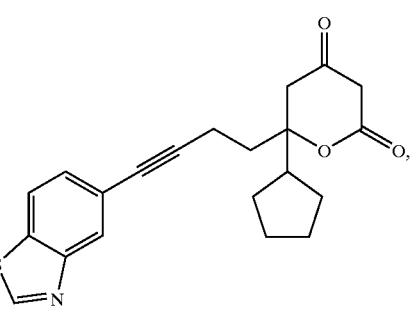
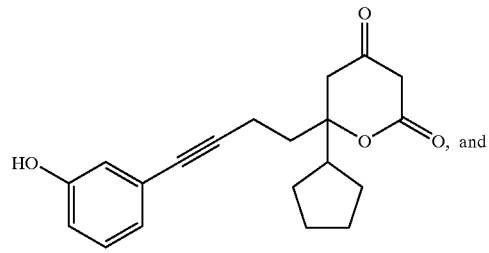
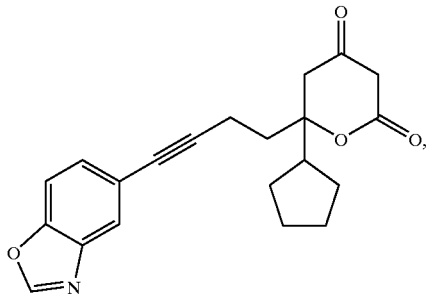
and pharmaceutically acceptable salts, prodrugs, active metabolites and solvates thereof.
Even more preferred compounds of the invention of formula I include:

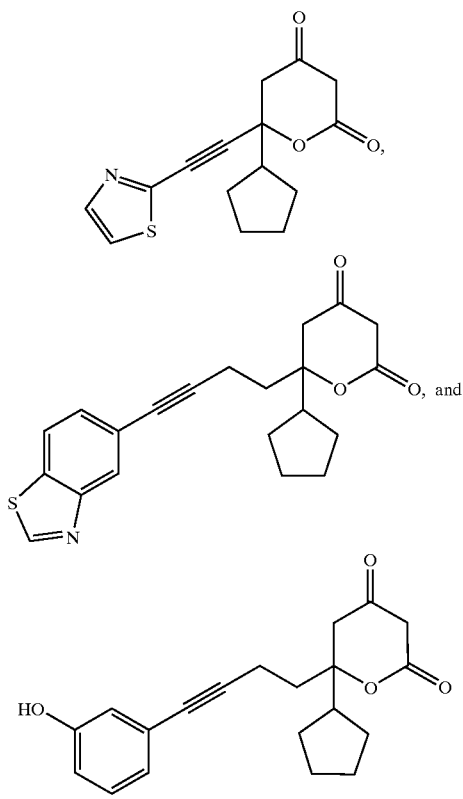

and pharmaceutically acceptable salts, prodrugs, active metabolites and solvates thereof.

The present invention is also directed to a method of inhibiting HCV RdRp activity, comprising contacting the protein with an effective amount of a compound of formula I, or a pharmaceutically acceptable salt, prodrug, pharmaceutically active metabolite, or solvate thereof. For example, HCV activity may be inhibited in mammalian tissue by administering a HCV-inhibiting agent according to the invention.

"Treating" or "treatment" is intended to mean at least the mitigation of an injury or a disease condition in a mammal, such as a human, that is alleviated by the inhibition of HCV activity, and includes: (a) prophylactic treatment in a mammal, particularly when the mammal is found to be predisposed to having the disease condition but not yet diagnosed as having it; (b) inhibiting the disease condition; and/or (c) alleviating, in whole or in part, the disease condition.

The activity of the inventive compounds as inhibitors of HCV activity may be measured by any of the suitable methods available in the art, including in vivo and in vitro assays. An example of a suitable assay for activity measurements is the HCV polymerase inhibition assay described herein.

Administration of the compounds of formula I and their pharmaceutically acceptable prodrugs, salts, active metabolites, and solvates may be performed according to any of the accepted modes of administration available to those skilled in the art. Illustrative examples of suitable modes of administration include oral, nasal, parenteral, topical, transdermal, and rectal. Oral and intravenous deliveries are preferred.

An HCV-inhibiting agent may be administered as a pharmaceutical composition in any suitable pharmaceutical form. Suitable pharmaceutical forms include solid, semisolid, liquid, or lyopholized formulations, such as tablets, powders, capsules, suppositories, suspensions, liposomes, and aerosols. The HCV-inhibiting agent may be prepared as a solution using any of a variety of methodologies. For example, the HCV-inhibiting agent can be dissolved with acid (e.g., 1 M HCl) and diluted with a sufficient volume of a solution of 5% dextrose in water (D5W) to yield the desired final concentration of HCV-inhibiting agent (e.g., about 15 mM). Alternatively, a solution of D5W containing about 15 mM HCl can be used to provide a solution of the HCV-inhibiting agent at the appropriate concentration. Further, the HCV-inhibiting agent can be prepared as a suspension using, for example, a 1% solution of carboxymethylcellulose (CMC).

Acceptable methods of preparing suitable pharmaceutical forms of the pharmaceutical compositions are known or may be routinely determined by those skilled in the art. For example, pharmaceutical preparations may be prepared following conventional techniques of the pharmaceutical chemist involving steps such as mixing, granulating, and compressing when necessary for tablet forms, or mixing, filling, and dissolving the ingredients as appropriate, to give the desired products for oral, parenteral, topical, intravaginal, intranasal, intrabronchial, intraocular, intraaural, and/or rectal administration.

Pharmaceutical compositions of the invention may also include suitable excipients, diluents, vehicles, and carriers, as well as other pharmaceutically active agents, depending upon the intended use. Solid or liquid pharmaceutically acceptable carriers, diluents, vehicles, or excipients may be employed in the pharmaceutical compositions. Illustrative solid carriers include starch, lactose, calcium sulfate dihydrate, terra alba, sucrose, talc, gelatin, pectin, acacia, magnesium stearate, and stearic acid. Illustrative liquid carriers include syrup, peanut oil, olive oil, saline solution, and water. The carrier or diluent may include a suitable prolonged-release material, such as glyceryl monostearate or glyceryl distearate, alone or with a wax. When a liquid carrier is used, the preparation may be in the form of a syrup, elixir, emulsion, soft gelatin capsule, sterile injectable liquid (e.g., solution), or a nonaqueous or aqueous liquid suspension.

A dose of the pharmaceutical composition contains at least a therapeutically effective amount of the HCV-inhibiting agent and preferably is made up of one or more pharmaceutical dosage units. The selected dose may be administered to a mammal, for example, a human patient, in need of treatment mediated by inhibition of HCV activity, by any known or suitable method of administering the dose, including topically, for example, as an ointment or cream; orally; rectally, for example, as a suppository; parenterally by injection; intravenously; or continuously by intravaginal, intranasal, intrabronchial, intraaural, or intraocular infusion. When the composition is administered in conjunction with a cytotoxic drug, the composition can be administered before, with, and/or after introduction of the cytotoxic drug. However, when the composition is administered in conjunction with radiotherapy, the composition is preferably introduced before radiotherapy is commenced.

The phrases "therapeutically effective amount" and "effective amount" are intended to mean the amount of an inventive agent that, when administered to a mammal in need of treatment, is sufficient to effect treatment for injury or disease conditions alleviated by the inhibition of HCV activity, such as for potentiation of anti-cancer therapies or inhibition of neurotoxicity consequent to stroke, head trauma, and neurodegenerative diseases. The amount of a given compound of the invention that will be therapeutically effective will vary depending upon factors such as the particular compound; the disease condition and the severity thereof, the identity and characteristics of the mammal in need thereof, which amount may be routinely determined by artisans.

It will be appreciated that the actual dosages of the HCV-inhibiting agents used in the pharmaceutical compositions of this invention will be selected according to the properties of the particular agent being used, the particular composition formulated, the mode of administration and the particular site, and the host and condition being treated. Optimal dosages for a given set of conditions can be ascertained by those skilled in the art using conventional dosage-determination tests. For oral administration, e.g., a dose that may be employed is from about 0.001 to about 1000 mg/kg body weight, preferably from about 0.1 to about 100 mg/kg body weight, and even more preferably from about 1 to about 50 mg/kg body weight, with courses of treatment repeated at appropriate intervals.

EXAMPLES

Specific examples of various compounds according to the invention may be advantageously prepared as set out in the examples below.

The structures of the compounds of the following examples were confirmed by one or more of the following: proton magnetic resonance spectroscopy, infrared spectroscopy, elemental microanalysis, mass spectrometry, thin layer chromatography, melting point, boiling point, and HPLC.

Proton magnetic resonance ($^1$H NMR) spectra were determined using a 300 megahertz Tech-Mag, Bruker Avance 300DPX, or Bruker Avance 500 DRX spectrometer operating at a field strength of 300 or 500 megahertz (MHz). Chemical shifts are reported in parts per million (ppm, δ) downfield from an internal tetramethylsilane standard. Alternatively, $^1$H NMR spectra were referenced to residual protic solvent signals as follows: CHCl$_3$=7.26 ppm; DMSO=2.49 ppm; C$_6$HD$_5$=7.15 ppm. Peak multiplicities are designated as follows: s=singlet; d=doublet; dd=doublet of doublets; t=triplet; q=quartet; br=broad resonance; and m=multiplet. Coupling constants are given in Hertz. Infrared absorption (IR) spectra were obtained using a Perkin-Elmer 1600 series FTIR spectrometer. Elemental microanalyses were performed by Atlantic Microlab Inc. (Norcross, Ga.) and gave results for the elements stated within ±0.4% of the theoretical values. Flash column chromatography was performed using Silica gel 60 (Merck Art 9385). Analytical thin layer chromatography (TLC) was performed using pre-coated sheets of Silica 60 F$_{254}$ (Merck Art 5719). HPLC chromatographs were run on a Hewlett Packard Model 1100 system fitted with a Zorbax SB-C18 4.6 mm×150 mm column having 3.5 micron packing material. Unless otherwise stated, a ramp of 5% CH$_3$CN/H$_2$O to 95% CH$_3$CN/H$_2$O over 7.5 minutes then holding at 95% CH$_3$CN/H$_2$O for 2.5 minutes (both solvents contained 0.1% v/v TFA) at a flow of 1 ml/min was used. Retention times (Rt) are given in minutes. Semi-preparative HPLC were run on a Gilson LC3D system fitted with a 21.2 mm×250 mm C8 column. Ramps were optimized for each compound with a CH$_3$CN/H$_2$O solvent system. Melting points (abbreviated as mp) were determined on a Mel-Temp apparatus and are uncorrected. All reactions were performed in septum-sealed flasks under a slight positive pressure of argon, unless otherwise noted. All commercial reagents were used as received from their respective suppliers with the following exceptions: tetrahydrofuran (THF) was distilled from sodium-benzophenone ketyl prior to use; dichloromethan (CH$_2$Cl$_2$) was distilled from calcium hydride prior to use; anhydrous lithium chloride was prepared by heating at 110° C. under vacuum overnight. Mass spectra, both low and high resolution, were measured using either electrospray (EI) or fast atom bombardment (FAB) ionization techniques.

The following abbreviations are used herein: E1$_2$O (diethyl ether); DMF (N,N-dimethylformamide); DMSO (dimethylsulfoxide); MeOH (methanol); EtOH (ethanol); EtOAc (ethyl acetate); Ac (acetyl); Hex (hexane); Me (methyl); Et (ethyl); Ph (phenyl); DIEA (diisopropylethylamine); TFA (trifluoroacetic acid); DTT (dithiothreitol); and THF (tetrahydrofuran).

Solid-phase syntheses were performed by immobilizing reagents with Rink amide linkers (Rink, *Tetrahedron Letters* (1987) 28:3787), which are standard acid-cleavable linkers that upon cleavage generate a free carboxamide group. Small-scale solid-phase syntheses, e.g., about 2–5 μmole, were performed using Chiron SynPhase® polystyrene O-series crowns (pins) derivatized with Fmoc-protected Rink amide linkers. For larger scale (e.g., greater than about 100 μmole) syntheses, the Rink amide linkages were formed to Argonaut Technologies Argogel® resin, a grafted polystyrene-poly(ethylene glycol) copolymer. Any suitable resin may be used as the solid phase, selected from resins that are physically resilient and that, other than with regard to the linking and cleavage reactions, are inert to the synthetic reaction conditions.

Example 1

6-cyclopentyl-6-[(4-methoxyphenyl)ethynyl] dihydro-2H-pyran-2,4(3H)-dione

Step 1: 6-(2-cyclopentyl-2-hydroxy-4-trimethylsilanyl-but-3-ynyl)-2,2-dimethyl-[1,3]dioxin-4-one

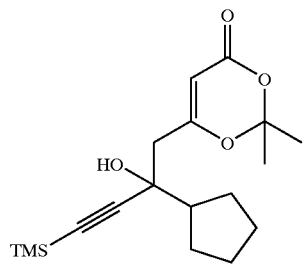

A solution of diisopropylamine (3.85 mL, 27.5 mmol) dissolved in THF (100 mL; dry) was cooled to −78° C., where BuLi (11 mL, 27.5 mmol; 2.5 M in hexanes) was added dropwise over 10 minutes. After stirring at this temperature for 5 minutes, the mixture was warmed to room temperature for 5 minutes, then cooled back to −78° C., where 2,2,6-trimethyl-[1,3]dioxin-4-one (3.60 mL, 27.5 mmol)(available from Aldrich) was added dropwise over 5 minutes, then stirred an additional 30 minutes at −78° C. To this solution was added 1-cyclopentyl-3-trimethylsilanyl-propynone (4.85 g, 25 mmol), which was prepared as described in *J. Org. Chem.*, 106:4786–4800 (1984) ($^1$H NMR (CDCl$_3$): δ0.24 (s, 9H), 1.63 (m, 4H), 1.90 (m, 4H), 2.92 (pentet, 1H, J=8.2 Hz)), over 5 minutes. The resulting mixture was stirred at −78° C. for 1 hour, then slowly warmed to −30° C. and quenched with 0.5 N citric acid. The mixture was diluted with ether, extracted with 1 N NaHCO$_3$, brine, and then dried with MgSO₄. This material (9.38 g), which contained unreacted 2,2,6-trimethyl-[1,3]dioxin-4-one, was used in the next step without further purification. ¹H NMR (CDCl₃): δ0.15 (s, 9H), 1.60 (m, 4H), 1.72 (s, 3H),2.01 (s, 1H), 2.14 (pentet, 1H), 2.47 (s, 1H), 2.55 (s, 2H), 5.40 (s, 1H); ESIMS (M+Na⁺): 359.1.

Step 2: 6-(2-cyclopentyl-2-hydroxy-but-3-ynyl)-2,2-dimethyl-[1,3]dioxin-4-one

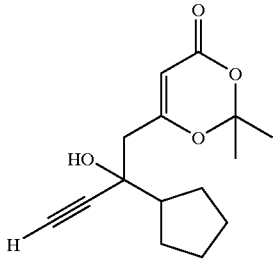

A solution of 6-(2-cyclopentyl-2-hydroxy-4-trimethylsilanyl-but-3-ynyl)-2,2-dimethyl-[1,3]dioxom-4-one (−27.5 mmol, crude material from step 1 above), CsF (7.6 g, 50.0 mmol), and MeOH (75 mL) was stirred at room temperature overnight. HPLC at this time still showed starting material, so the reaction was heated at 40° C. for an additional 4 hours, at which time all starting material had been consumed. The reaction was concentrated and purified by flash chromatography through silica, eluted with 30% ethylacetate/hexanes, yielding 4.0 g of product (61% yield for two steps). ¹H NMR (CDCl₃): δ 1.63 (m, 4H), 1.72 (s, 3H), 1.74 (s, 3H), 2.16 (m, 1H), 2.49 (s, 1H), 2.53 (s, 1H), 2.58 (s, 1H), 5.43 (s, 1H), ESIMS (M+Na⁺): 287.1.

Step 3: 6-[2-cyclopentyl-2-hydroxy-4-(4-methoxyphenyl)-but-3-ynyl]-2,2-dimethyl-[1,3]dioxin-4-one

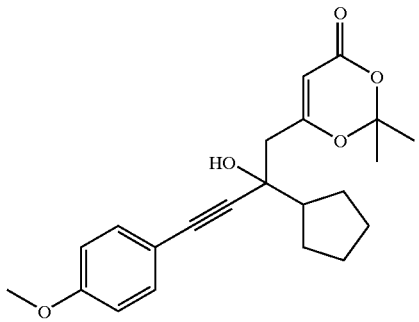

To a solution of 6-(2-cyclopentyl-2-hydroxy-but-3-ynyl)-2,2-dimethyl-[1,3]dioxin-4-one (66 mg, 0.25 mmol), 4-bromoanisole (34.4 μL, 0.275 mmol), diisopropylamine (42.4 μL, 0.30 mmol), P(t-Bu)₃ (30 μL of 10% by weight solution in hexanes, 0.015 mmol), and anhydrous dioxane (220 μL), under argon, was added Pd(PhCN)₂Cl₂ (2.87 mg, 0.0075 mmol), and CuI (0.95 mg, 0.005 mmol), at room temperature. The reaction was vacuum-flushed with argon (3×), then stirred at room temperature for 2.5 hours. HPLC at this time indicated ~60% conversion. The reaction was then placed in a 35° C. oil bath for an additional 2 hours, at which time all starting material had been consumed. The reaction was concentrated and purified by silica gel chromatography-eluted with 30% ethytacetate/hexanes, which gave 62 mg of the product (67% yield). ¹H NMR (CDCl₃): δ 1.63 (m, 4H), 1.72 (s, 3H), 1.73 (s, 3H), 2.23 (pentet, 1H, J=8.0 Hz), 2.54(s, 1H), 2.65 (s, 2H), 3.81 (s, 3H), 5.47 (s, 1H), 6.83 (d, 2H, J=8.7 Hz), 7.31 (d, 2H, J=8.1 Hz); ESIMS (M+Na⁺): 393.2.

Step 4: 6-cyclopentyl-6-[(4methoxyphenyl)ethynyl]dihydro-2H-pyran-2,4(3H)-dione

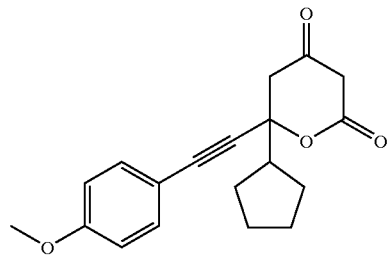

A solution of 6-[2-cyclopentyl-2-hydroxy-4-(4-methoxyphenyl)-but-3-ynyl]-2,2-dimethyl-[1,3]dioxin-4-one (55 mg, 0.1485 mmol), 1NaOH n(150 μL, 0.1485 mmol), and MeOH (1.5 mL), was stirred at room temperature for 2 hours, at which time HPLC indicated that all starting material had been consumed. The reaction was quenched with 0.5 N citric acid, and extracted with ethylacetate. The organic layer was dried with MgSO₄, concentrated and purified by preparative HPLC, giving 13 mg of the product (24% yield). ¹H NMR (CDCl₃): δ 1.73 (m, 4H), 2.23 (pentet, 1H, J=8.1 Hz), 2.85 (d, 1H, J=16.3 Hz), 2.95 (d, 1H, J=16.5 Hz), 3.45 (d, 1H, J=21.5 Hz), 3.85 (s, 3H), 3.98 (d, 1H, J=22.0 Hz), 6.84 (d, 2H, J=8.7 Hz), 7.32 (d, 2H, J=8.1 Hz); ESIMS (M+Na⁺): 335.1.

Example 2

Cyclopentyl-6-(1,3-thiazol-2-ylethynyl)dihydro-2H-pyran-2,4(3H)-dione

Step 1: 6-(2-cyclopentyl-2-hydroxy-4-thiazol-2-yl-but-3-ynyl)-2,2-dimethyl-[1,3]dioxin-4-one

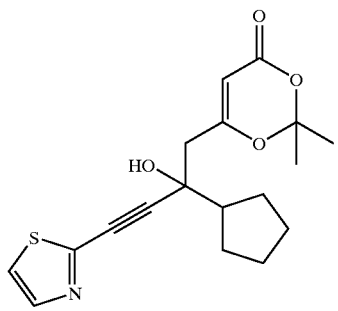

To a degassed solution of 6-(2-cyclopentyl-2-hydroxy-but-3-ynyl)-2,2-dimethyl-[1,3]dioxin-4-one (264.1 mg, 1.0; prepared as described in Example 1, Step 2), 2-bromothiazole (99.1 μL, 1.1 mmol), diisopropylamine (1.5 mL), and DMF (0.5 mL), under argon, was added Pd(PPh₃)₂Cl₂ (28.1 mg, 0.04 mmol) and CuI (15.2 mg, 0.08 mmol). The resulting mixture was vacuum-flushed with argon (3×), then placed in 100° C. oil bath for 5 minutes, during which time the reaction becomes black/brown in color. The mixture was filtered through a plug of silica eluted with ethylacetate, concentrated, and purified by flash chromatography using 30% EtOAc/Hex as the eluent. The yield of product was 280 mg (81% yield). ¹H NMR (CDCl₃): δ 1.63 (m, 4H), 1.72 (s, 3H), 1.73 (s, 3H), 2.23 (pentet, 1H, J=8.0 Hz), 2.54 (s, 1H), 2.65 (s, 2H), 3.81 (s, 3H), 5.47 (s, 1H), 6.83 (d, 2H, J=8.7 Hz), 7.31(d, 2H, J=8.1 Hz), ESIMS (M+Na⁺): 393.2.

Step 2: Cyclopentyl-6-(1,3-thiazol-2-ylethynyl)dihydro-2H-pyran-2,4(3H)-dione

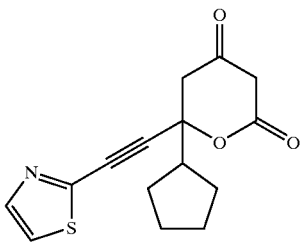

The title compound was prepared analogously to example 1, except 6-(2-cyclopentyl-2-hydroxy-4-thiazol-2-yl-but-3-ynyl)-2,2-dimethyl-[1,3]dioxin-4-one (from Step 1) was used rather than 6-[2-cyclopentyl-2-hydroxy-4-(4-methoxyphenyl)-but-3-ynyl]-2,2-dimethyl-[1,3]dioxin-4-one. $^1$H NMR (CDCl$_3$): δ 1.63–2.05 (bm, 4H), 2.23 (pentet, 1H, J=8.1 Hz), 2.78 (d, 1H, J=17.7 Hz), 3.04 (d, 1H, J=17.7 Hz), 3.51 (d, 1H, J=20.0 Hz), 3.97 (d, 1H, J=20.0 Hz), 7.46 (d, 1H, J=3.2 Hz), 7.89 (d, 2H, J=3.4 Hz). Anal. Calcd. for C$_{15}$H$_{15}$N$_1$O$_3$S$_1$.0.25 H$_2$O: C, 57.75; H, 4.93; N, 4.35. Found: C, 58.2; H, 5.34; N, 4.36; ESIMS (M+Na$^+$): 312.0.

Example 3

6-cyclopentyl-6-methyl-dihydro-pyran-2,4-dione

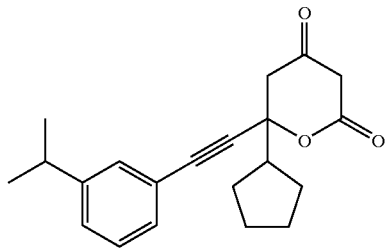

The title compound was prepared analogously to Example 1, except 3-bromobenzene was used in place of 4-bromoanisole in Step 3 of that example. $^1$H NMR (CDCl$_3$): δ 1.24 (d, 6H, J=7.0 Hz), 1.55–2.05 (bm, 4H), 2.45 (pentet, 1H, J=8.3 Hz), 2.74 (d, 1H, J=17.5 Hz), 2.45 (m, 1H), 3.00 (d, 1H, J=17.5 Hz), 3.47 (d, 1H, J=19.8 Hz), 3.97 (d, 1H, J=19.8 Hz), 7.46 (m, 4H). Anal. Calcd. For C$_{21}$H$_{24}$O$_3$.0.15 H$_2$O: C, 77.1; H, 7.49. Found: C, 77.14; H, 7.63; ESIMS (M–H$^-$): 323.2.

Example 4

6-cyclopentyl-6-methyl-dihydro-pyran-2,4-dione

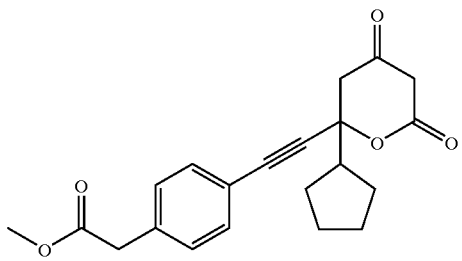

The title compound was prepared analogously to Example 1, except (4-bromo-phenyl)-acetic acid methyl ester was used in place of 4-bromoanisole in Step 3 of that example. $^1$H NMR (CDCl$_3$): δ 1.51–2.15 (bm, 4H), 2.44 (pentet, 1H, J=8.3 Hz), 2.74 (d, 1H, J=17.3 Hz), 3.00 (d, 1H, J=17.5 Hz), 3.47 (d, 1H, J=19.7 Hz), 3.97 (d, 1H, J=19.8 Hz), 7.25 (d, 1H, J=7.2 Hz), 7.36 (d, 1H, J=8.1 Hz). Anal. Calcd. for C$_{21}$H$_{24}$O$_3$.0.15 H$_2$O: C, 77.1; H, 7.49. Found: C, 77.14; H, 7.63; ESIMS (M–H$^-$): 353.1.

Example 5

6-but-3-ynyl-6-cyclopentyl-dihydro-pyran-2,4-dione

Step 1: (4-bromobut-1-ynyl)trimethylsilane

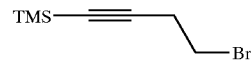

The title compound was prepared as described in the *J. Amer. Chem. Soc.,* 5383–5396 (1988).

Step 2: 1-cyclopentyl-5-trimethylsilanyl-pent-4-yn-1-one

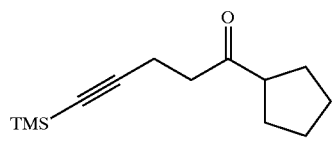

To a solution of (4-bromobut-1-ynyl)trimethylsilane (8.0 g, 39 mmol), from Step 1, in THF (50 mL) was added magnesium turnings (1.14 g, 47 mmol), and iodine (10 mg). The reaction was stirred for one hour at 24° C., and then warmed in an oil bath at 50° C. for one hour, then allowed to cool to 24° C. To the solution, cyclopentanecarboxylic acid methoxy-methyl-amide (6.12 g, 39 mmol) in THF (30 mL) was added. After the reaction was stirred for 4 hours, 2 N HCl (50 mL) and EtOAc (50 mL) were added. The layers were separated, and the aqueous layer was extracted three times with 25 mL of EtOAc. The organic layers were combined and washed successively with 50 mL saturated sodium bicarbonate, 50 mL water, and 40 mL saturated NaCl. The organic layer was then dried with sodium sulfate. After filtering, the organic layer was concentrated using rotary evaporation, and then chromatographed (80 g Si, 3% EtOAc in hexanes) to yield the product (4.39 g, 51% yield). $^1$H NMR (CDCl$_3$): δ 0.13 (s, 9H), 1.70 (m, 8H), 2.49 (t, J=8.10 Hz, 2H), 2.69 (t, J=7.91 Hz, 2H), 2.88 (p, J=7.91 Hz, 1H).

Step 3: 6-but-3-ynyl-6-cyclopentyl-dihydro-pyran-2,4-dione

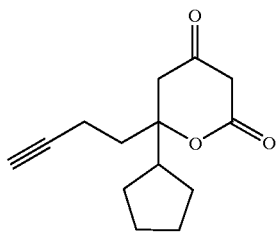

To a slurry of NaH (2.4 g, 59.3 mmol) in THF (250 mL) cooled to −50° C. was added methylacetoacetate (6.4 mL, 59.3 mmol), taking care to keep the solution below −25° C. The solution was stirred for 20 minutes, and then a solution of nBuLi (23.7 mL, 2.5 M in cyclopentane, 59.3 mmol) was added over a period of 20 minutes. The reaction was stirred for 40 minutes. A solution of 1-cyclopentyl-5-trimethylsilanyl-pent-4-yn-1-one from step 2 above, in 50 mL of THF, was added and stirred for 1.5 hours. The reaction was quenched with 50 mL of saturated $NH_4Cl$ and 50 mL of 2N HCl. The layers were separated, and the aqueous layer was acidified to a pH of 2 using concentrated HCl. The aqueous layer was extracted 3 times with 100 mL of EtOAc. The organic layers were combined and washed successively with 100 mL saturated $NH_4Cl$, 50 mL of water, and 50 mL of saturated NaCl. The organic layer was dried over $MgSO_4$, separated from the solids, and concentrated through rotary evaporation.

The crude organic product was then dissolved in 120 mL of MeOH, to which 6.0 grams of finely powdered $K_2CO_3$ (anhydrous) was added. The slurry was stirred at reflux for 1.5 hours, and then concentrated by rotary evaporation. The residue was dissolved in 100 mL of water and 50 mL of EtOAc. The layers were separated, and the organic product was extracted three times with 50 mL of 5% $K_2CO_3$ in water. The aqueous layers were combined, and acidified with concentrated HCl. The aqueous solution was extracted 3 times with 100 mL of $CH_2Cl_2$. The organics were combined and dried with $MgSO_4$. After filtering and concentrating, the organic product was chromatographed (80 g $SiO_2$, 50% EtOAc in hexanes) to yield the desired product (2.65 g, 58%). $^1H$ NMR ($CDCl_3$): δ 1.56 (m, 8H), 1.99 (m, 2H), 2.10 (s, 1H), 2.21 (p, J=7.91 Hz, 1H), 2.35 (dt, J=2.45 Hz, J=7.54 Hz, 2H), 2.77 (dd, J=13.00, J=16.01, 2H), 3.43 (s, 2H). Anal. Calcd. For $C_{14}H_{18}O_3$.0.1 $CH_2Cl_2$: C, 69.75; H, 7.56. Found C, 69.76; H, 7.65; ESIMS ($M+Na^+$): 257.

Example 6

6-cyclopentyl-6-(4-phenyl-but-3-ynyl)-dihydro-pyran-2,4-dione

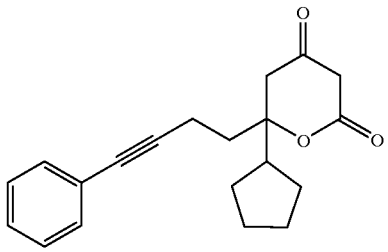

To a solution of 6-but-3-ynyl-6-cyclopentyl-dihydro-pyran-2,4-dione (100 mg, 0.42 mmol; prepared as described in Example 5), and iodobenzene (0.052 mL, 0.46 mmol) in a mixture of DMF (0.2 mL) and diisopropyl amine (0.6 mL), was added copper (I) iodide (6.4 mg, 0.034 mmol) and bis(triphenylphosphine) palladium (II) chloride (12 mg, 0.017 mmol). The mixture was sonicated for 2 minutes, and then heated at 90° C. for 5 minutes. The reaction was passed through a small plug of silica, and washed with EtOAc until the filtrate ran clear. Acetic acid (4 mL) was then passed through the silica, and washed with 5% acetic acid in EtOAc until the filtrate ran clear. The acidic layer was concentrated by rotary evaporation, and then chromatographed (8 g silica, 40% EtOAc in hexanes) to give the product (20 mg, 16%). $^1H$ NMR ($CDCl_3$): δ 1.70 (m, 8H), 2.04 (m, 2 H), 2.28 (p, J=9.23 Hz, 1H), 2.57 (t, J=7.16 Hz, 2H), 2.83 (dd, J=15.82 Hz, J=25.43 Hz, 2H), 3.45 (d, J=1.51 Hz, 2H), 7.29 (m, 3H), 7.38 (m, 2H). Anal. Calcd. For $C_{20}H_{22}O_3$.0.2 MeOH: C, 76.15; H, 7.28. Found C, 76.45; H, 7.68. ESIMS ($M+Na^+$): 333.

Example 7

6-Cyclopentyl-6-[4-(3-methoxy-phenyl)-but-3-ynyl]-dihydro-pyran-2,4-dione

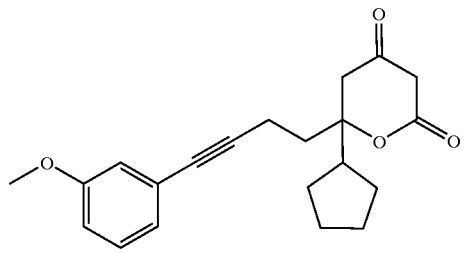

The title compound was prepared analogously to Example 6, except 3-iodoanisole was used for iodobenzene in Step 3 of that example. $^1H$ NMR ($CDCl_3$): δ 1.73 (m, 8H), 2.04 (t, J=7.54 Hz, 2H), 2.28 (p, J=9.04, 1H), 2.57 (t, J=7.72, 2H), 2.82 (dd, J=16.2 Hz, J=24.3 Hz, 2H), 3.44 (d, J=1.32 Hz, 2H), 3.80 (s, 3H), 6.85 (m, 1H), 6.96 (m, 2H), 7.19 (t, J=7.91 Hz, 1H). Anal. Calcd. For $C_{21}H_{24}O_4$.0.05 $CH_2Cl_2$: C, 73.35; H, 7.05. Found C, 73.40; H, 7.15; ESIMS ($M+Na^+$): 367.

Example 8

6-(4-Benzothiazol-5-yl-but-3-ynyl)-6-cyclopentyl-dihydro-pyran-2,4-dione

Step 1: 5-bromo-benzthiazole

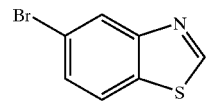

The title compound was prepared as described in the *J. Org. Chem:*, 1328–1331 (1976).

Step 2: 6-(4-Benzothiazol-5-yl-but-3-ynyl)-6-cyclopentyl-dihydro-pyran-2,4-dione

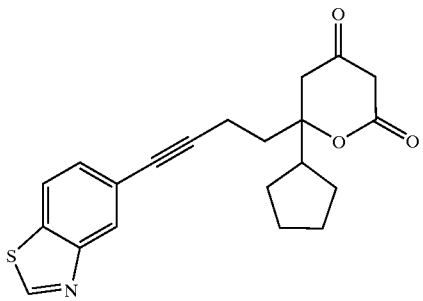

The title compound was prepared analogously to Example 6, except 5-bromo-benzthiazole (described below) was substituted for iodobenzene in Step 3 of that example. $^1H$ NMR ($CDCl_3$): δ 1.63 (m, 8H), 2.09 (dt, J=3.01 Hz, J=7.54 Hz, 2H), 2.30 (p, J=8.85, 1H), 2.61 (t, J=7.16 Hz, 2H), 2.85 (dd, J=17.71, J=n16.20, 2H), 3.48 (s, 2H), 7.53 (d, J=8.48 Hz, 1H), 7.91 (d, J=8.29, 1H), 8.21 (s, 1H), 9.23 (s, 1H), Anal. Calcd. For $C_{21}H_{21}NO_3S$. 1 TFA.0.1Hexane: C, 57.83; H, 4.81; N, 2.86; S, 6.54; found C, 57.63H, 5.19; N, 2.99; S, 6.41; ESIMS ($M+Na^+$): 390.

Example 9

6-Cyclopentyl-6-[4-(2,3-dihydro-benzo[1,4]dioxin-6-yl)-but-3-ynyl]-dihydro-pyran-2,4-dione

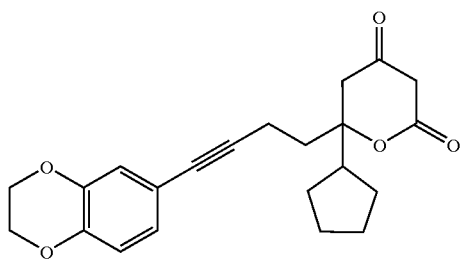

The title compound was prepared analogously to Example 6, except 3,4-ethylenedioxyiodobenzene was used for iodobenzene in Step 3 of that example $^1$H NMR (CDCl$_3$): δ 1.93 (m, 8H), 2.14 (t, J=7.34 Hz, 2H), 2.21 (p, J=9.14, 1H), 2.53 (t, J=7.42, 2H), 2.88 (dd, J=16.20 Hz, J=22.3 Hz, 2H), 3.43 (d, J=1.32 Hz, 2H), 3.80 (s, 3H), 4.21 (s, 4H), 6.75 (d, J=7.74, 1H), 6.92 (d, J=7.32, 1H), 7.09 (s, 1H), Anal. Calcd. For C$_{22}$H$_{24}$O$_5$: C, 71.72; H, 6.57. Found C, 71.98; H, 6.79; ESIMS (M+Na$^+$): 391.

Example 10

6-(4-Benzo[1,3]dioxol-5-yl-but-3-ynyl)-6-cyclopentyl-dihydro-pyran-2,4-dione

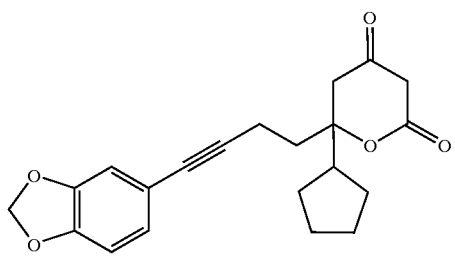

The title compound was prepared analogously to Example 6, except 1-iodo-3,4-methylenedioxybenzene was used for iodobenzene in Step 3 of that example. $^1$H NMR (CDCl$_3$) δ 1.65 (m, 8H), 2.00 (m, 3H), 2.54 (t, J=7.35 Hz, 2H), 2.82 (dd, J=16.20, J=24.30, 2H), 3.44 (d, J=1.51 Hz, 2H), 5.96 (s, 2H), 6.73 (d, J=8.10 Hz, 1H), 6.84 (d, J=1.32 Hz, 1H), 6.91 (dd, J=1.70 Hz, J=8.10 Hz, 1H). Anal. Calcd. For C$_{21}$H$_{22}$O$_5$.0.5 CH$_2$Cl$_2$: C, 66.18; H, 5.92. Found C, 66.16; H, 6.11; ESIMS (M+Na$^+$): 3.77.

Example 11

N-{5-[4-(2-Cyclopentyl-4,6-dioxo-tetrahydro-pyran-2-yl)-but-1-ynyl]-pyridin-2-yl}-acetamide Step 1: N-(5-bromo-pyridin-2-yl)-acetamide

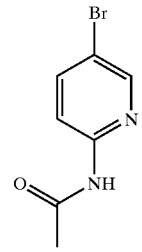

The title compound was prepared as described in Chem. Pharm. Bull., 523–527 (1966).

Step 2: N-{5-[4-(2-Cyclopentyl-4,6-dioxo-tetrahydro-pyran-2-yl)-but-1-ynyl]-pyridin-2-yl}-acetamide

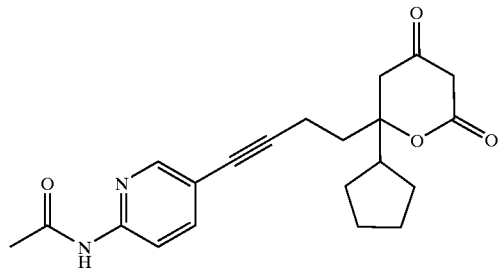

The title compound was prepared analogously to Example 6, except N-(5-bromo-pyridin-2-yl)-acetamide was used for iodobenzene in step 3 of that example. $^1$H NMR (CDCl$_3$): δ 1.61 (m, 8H), 2.04 (m, 2H), 2.21 (s, 3H), 2.29 (p, J=7.91 Hz, 1H), 2.57 (t, J=7.35 Hz, 2H), δ 2.80 (dd, J=16.01 Hz, J=10.36 Hz, 2H), δ 3.45 (s, 2H), δ 7.69 (dd, J=2.26 Hz, J=6.41 Hz, 1H), δ 8.04 (br, 1H), δ 8.14 (d, J=8.48 Hz, 1H), δ 8.27 (s, 1H). Anal. Calcd. For C$_{21}$H$_{24}$N$_2$O$_4$.0.25 EtOAc.0.2 CH$_2$Cl$_2$: C, 65.44; H, 6.53; N, 6.88. Found C, 65.73; H, 6.62; N, 6.49; ESIMS (M+Na$^+$): 391.

Example 12

{4-[4-(2-cyclopentyl-4,6-dioxo-tetrahydro-pyran-2-yl)-but-1-ynyl]-phenyl}-acetic acid methyl ester

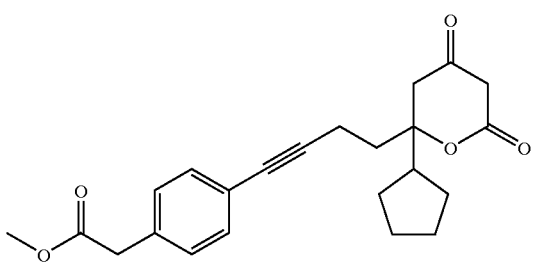

The title compound was prepared analogously to Example 6, except methyl 4-bromophenylacetate was used for iodobenzene in Step 3 of that example. $^1$H NMR (CDCl$_3$): δ 1.62 (m, 8H), 2.04 (m, 2H), 2.27 (p, J=8.85 Hz, 1H), 2.57 (t, J=7.16 Hz, 2H), 2.82 (dd, J=16.20 Hz, J=24.30 Hz, 2H), 3.45

(s, 2H), 3.61 (s, 2H), 3.69 (s, 3H), 7.21 (d, J=7.91 Hz, 2H), 7.35 (d, J=8.10 Hz, 2H). Anal. Calcd. For $C_{23}H_{26}O5.0.1$ $CH_2Cl_2$: C, 70.97; H, 6.76. Found C, 71.20; H, 6.81. ESIMS (MFdD-1): 381.

Example 13

6-Cyclopentyl-6-[4-(3-hydroxy-phenyl)-but-3-ynyl]-dihydro-pyran-2,4-dione

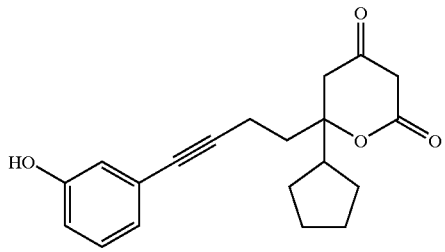

The title compound was prepared analogously to Example 6, except 3-iodophenol was used for iodobenzene in Step 3 of that example. $^1$H NMR (CDCl$_3$): δ 1.60 (m, 8H), 2.04 (dd, J=3.77 Hz, J=6.59 Hz, 2H), 2.27 (p, J=8.10 Hz, 1H), 2.57 (t, J=7.16 Hz, 2H), 2.84 (dd, J=16.20 Hz, J=25.06 Hz, 2H), 3.45 (s, 2H), 6.77 (dd, J=2.45 Hz, J=8.10 Hz, 1H), 6.86 (s, 1H), 6.95 (d, J=6.97, 1H), 7.16 (t, J=8.10 Hz, 1H). Anal. Calcd. For $C_{20}H_{22}O_4.0.05$ $CH_2Cl_2$: C, 72.83; H, 6.74. Found C, 72.60; H, 6.71; ESIMS (M+Na$^+$): 349.

Example 14

6-(4-benzooxazol-5-yl-but-3-ynyl)-6-cyclopentyl-dihydro-pyran-2,4-dione

Step 1: 5-iodo-benzoxazole

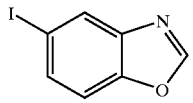

The title compound was prepared as described in *Org. Prep. Proced. Int.,* 613–18 (1990).

Step 2: 6-(4-benzooxazol-5-yl-but-3-ynyl)-6-cyclopentyl-dihydro-pyran-2,4-dione

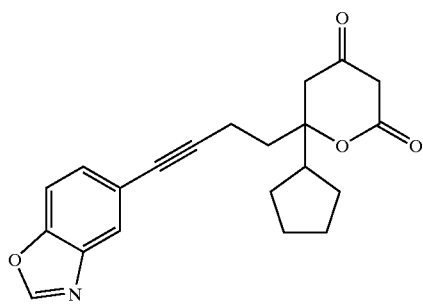

The title compound was prepared analogously to Example 6, except 5-iodo-benzoxazole was used for iodobenzene in Step 3 of that example. $^1$H NMR (CDCl$_3$): δ 1.50 (m, 9H), 2.12 (t, J=7.35 Hz, 2H), 2.90 (t, J=7.16 Hz, 2H), 5.00 (s, 1H), 6.90 (s, 1H), 7.75 (d, J=8.67 Hz, 1H), 8.15 (d, J=10.36 Hz, 1H), 8.52 (s, 1H), 11.42 (s, 1H). Anal. Calcd. For $C_{21}H_{21}NO_4.0.7$ TFA.0.1 $CH_2Cl_2$: C, 60.96; H, 5.07N, 3.16. Found C, 60.69; H, 5.52; N, 3.47; ESIMS (M+Na$^+$): 374.

Example 15

6-cyclopentyl-4-ethoxy-6-[4-(3-hydroxy-phenyl)-but-3-ynyl]-5,6-dihydro-pyran-2-one

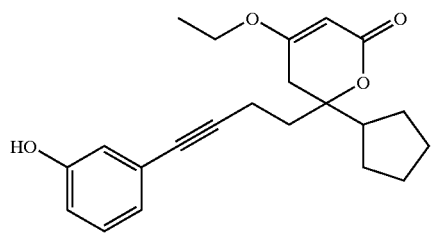

The title compound was prepared analogously to Example 6, except 3-iodophenol was used for iodobenzene, and 6-but-3-ynyl-6-cyclopentyl-4-ethoxy-5,6-dihydro-pyran-2-one, described in Step 2 of that example, was used for 6-but-3-ynyl-6-cyclopentyl-dihydro-pyran-2,4-dione. $^1$H NMR (CDCl$_3$): δ 1.26 (t, 2H, J=7.16 Hz), δ 1.51–1.81 (m, 8H), δ 2.10 (t, 2H, J=7.54 Hz), δ 2.36 (t, 1H, J=8.10 Hz), δ 2.48 (d, 1H, J=17.71 H), δ 2.52 (t, 2H, J=7.35 Hz), δ 2.68 (d, 1H, J=17.52 Hz), δ 3.94 (q, 2H, J=7.35 Hz), δ 5.14 (d, 2H, J=6.22 Hz), δ 6.77 (dd, 1H, J=5.65 Hz, J=2.45 Hz), δ 6.87 (s, 1H), δ 6.95 (d, 1H, J=6.59 Hz), δ 7.14 (t, 1H, J=7.91 Hz). Anal. Calcd. For $C_{22}H_{26}O_4$ 0.3 EtOAc: C, 73.16, H 7.52. Found: C, 73.18, H, 7.57; ESIMS (M+Na$^+$) 377.1.

Example 16

6-But-3-ynyl-6-cyclopentyl-3-phenylsulfanyl-dihydro-pyran-2,4-dione

Step 1: 6-But-3-ynyl-3-chloro-6-cyclopentyl-dihydro-pyran-2,4-dione

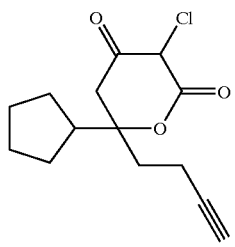

To a slurry of sodium hydride (480 mg, 60% suspension in mineral oil, 12 mmol) in THF (30 mL) cooled to −10° C. was added ethyl-2-chloroacetoacetate (1.66 mL, 12 mmol). The reaction was stirred until all gas evolution ceased. The reaction was then cooled to −40 ° C. and a solution of butyl lithium (4.8 mL, 2.5 M in ether, 12 mmol) was added. The reaction was stirred for 10 minutes, and then 1-cyclopentyl-pent-4-yn-1-one (0.60 g, 4 mmol) was added as a solution in THF (10 mL). The reaction was stirred for 1 hour, and then quenched with 40 mL saturated ammonium chloride. The solution was acidified further with 5 mL of 6 N HCl. The layers were separated, and the aqueous was extracted with ethyl acetate. The organics were combined and washed with water and then saturated sodium chloride. The organic phase was dried over sodium sulfate, filtered, and then concentrated. The crude product was then dissolved in toluene (13 mL) and bis(dibutylchlorotin) (1.027 g) was added. The solution was heated to reflux for one hour. The reaction was then concentrated and chromatographed (40 g silica gel, 2% MeOH in $CH_2Cl_2$) to yield the title compound (0.820 g, 76%).

Step 2: 6-But-3-ynyl-6-cyclopentyl-3-phenylsulfanyl-dihydro-pyran-2,4-dione

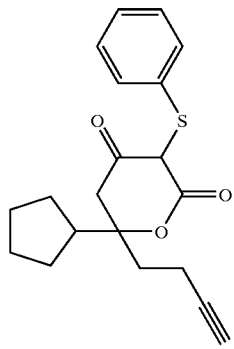

A solution of thiophenol (0.23 mL, 2.2 mmol), triethyl amine (0.156 mL, 1.1 mmol), and 6-but-3-ynyl-3-chloro-6-cyclopentyl-dihydro-pyran-2,4-dione (0.30 g, 1.1 mmol; prepared as described in step 1 above) in DMF (3 mL) was stirred at room temperature for 2 hours. The reaction was then concentrated by rotary evaporation, and then chromatographed (40 g silica gel, gradient elution from 40% EtOAc/Hexanes to 75% EtOAc/Hexanes) to yield the title compound (135 mg, 36%). $^1$H NMR (CDCl$_3$): δ1.31–1.80 (m, 9H); δ1.96–2.00 (m, 2 H); δ2.03–2.11 (3H, m); δ2.85 (2H, dd, J1=17.94, J2=27.03); δ7.13–7.36 (5H, m). Anal. Calcd. for C$_{20}$H$_{22}$O$_3$S.0.1 MeOH.0.15 CH$_2$Cl$_2$: C, 67.86; H, 6.38; S, 8.95. Found C, 68.08; H, 6.48; S, 8.52. ESIMS (M+Na$^+$): 365.

Example 17

6-Cyclopentyl-6-[4-(3-hydroxy-phenyl)-but-3-ynyl]-3-phenylsulfanyl-dihydro-pyran-2,4-dione

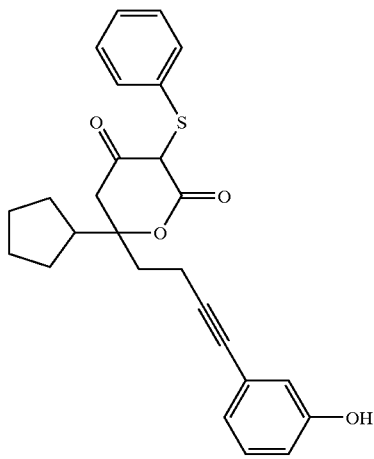

The title compound was prepared analogously to Example 6 using 6-but-3-ynyl-6-cyclopentyl-3-phenylsulfanyl-dihydro-pyran-2,4-dione (described in Example 16) in place of 6-but-3-ynyl-6-dihydro-pyran-2,4-dione and 3-bromophenol in place of iodobenzene. $^1$H NMR (CDCl$_3$): δ1.40–1.82 (m, 8H); δ2.14 (t, 1H, J=7.58 Hz); δ2.21–2.33 (m, 2H); δ0.40–2.56 (m, 2H); δ0.92 (dd, J1=17.94 Hz, J2=22.99 Hz, 2H); δ0.06–7.56 (m, 9H). Anal. Calcd. for C$_{26}$H$_{26}$O$_4$S.0.2 AcOH. 1 MeCN: C, 69.95; H, 6.16; S, 6.85. Found C, 70.23; H, 6.58; S, 6.09. ESIMS (M+Na$^+$): 457.

HCV Polymerase Inhibition Assay

The above-described compounds were tested for activity with HCV polymerase. Recombinant HCV polymerase was tested for its ability to perform primer/template-directed transcription in assays that contained 30 mM tris-HCl pH 7.2, 10 mM MgCl$_2$, 20 mM NaCl, 1 mM Dithiothreitol (DTT), 0.05% Tween-20, 1% glycerol, 5 pmoles biotin-dG$_{12}$ (primer), 0.5 pmoles poly(rC)$_{300}$ (template), 1 μM GTP, 0.1–0.3 uCi α-$^{32}$P-GTP, and 2.5 pmoles (0.15 μg) HCV polymerase protein in a final volume of 75 μL. Reactions were initiated by addition of enzyme and incubated 30 minutes at 30° C. Reactions were stopped by addition of 33 mM EDTA, and polynucleotide products were collected by filtration through Diethylaminoethyl (DE) Filtermat papers (Wallac). Unincorporated triphosphate was removed by washing the filters with 5% dibasic sodium phosphate. The filters were counted in a Packard Tri-Lux Microbeta scintillation counter (Packard Bioscience, Meriden, Conn.). Compounds to be tested were added at various concentrations, e.g., 1 μm to 50 μm, from stocks in 10% DMSO-water (final DMSO is 1% in reaction).

IC$_{50}$ values were estimated from the primary cpm data (collected in triplicate) using the formula: cpm (I)=cpm (no inhibitor)(1−([I]/([I]+IC$_{50}$))). An IC$_{50}$ value represents the concentration (in μM) of a compound that provides 50% inhibition of polymerase-directed transcription in the above assay. A percent inhibition value is expressed for a compound where it was impractical to calculate an IC$_{50}$ value with available data. If the IC$_{50}$ estimated by the above equation was less than 200 nM, it was recalculated using the following equation, which takes into account the enzyme concentration (30 nM) in the assay: cpm(I)=cpm(no inhibitor)(1−((((I+IC$_{50}$+30e−9)−sqrt(((I+IC$_{50}$+30e−9)$^2$)−4× 30e−9×1)))/((2) (30e−9))). Curve fitting was performed using the program KaleidaGraph (Synergy Software, Reading, Pa.).

Inhibition concentration (IC$_{50}$) values as determined for exemplary compounds of the invention are presented in Table 1 below.

TABLE 1
HCV Polymerase Inhibition Assay
| Example Number | Structure | IC$_{50}$ ($\mu$M) |
| --- | --- | --- |
| 1 | 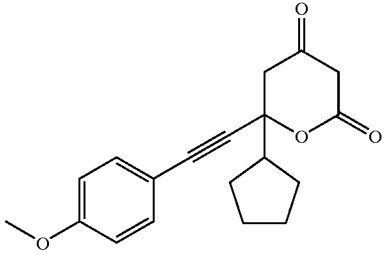 | 12 |
| 2 | 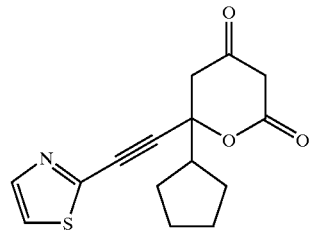 | 2.1 |
| 3 | 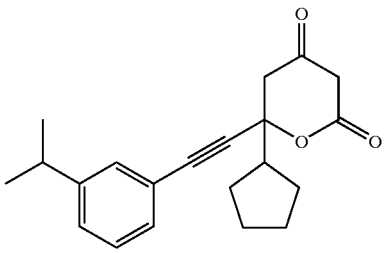 | 8.5 |
| 4 | 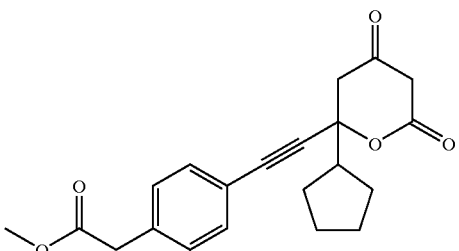 | 64.6 |
| 5 | 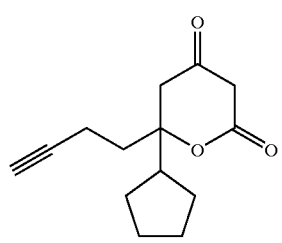 | 74 |
| 6 | 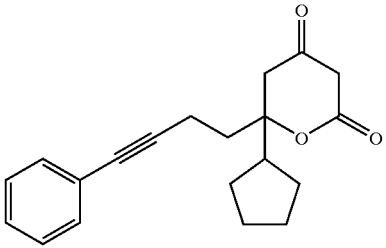 | 8.29 |

TABLE 1-continued
HCV Polymerase Inhibition Assay
| Example Number | Structure | IC$_{50}$ ($\mu$M) |
|---|---|---|
| 7 | 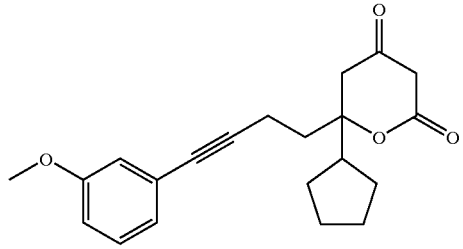 | 12.1 |
| 8 | 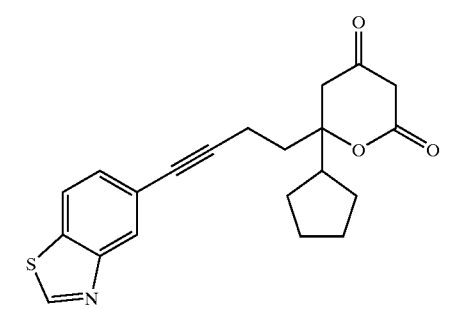 | 4.5 |
| 9 | 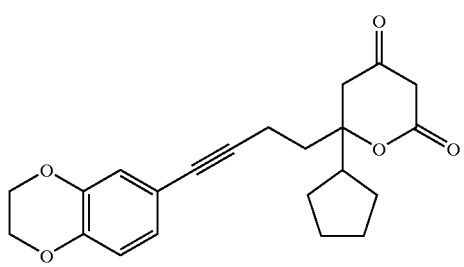 | 11.7 |
| 10 | 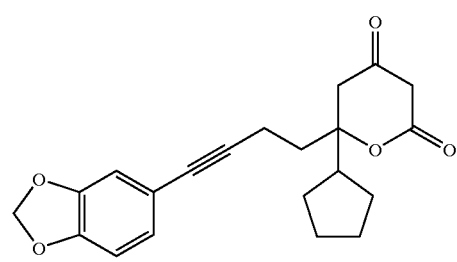 | 10.7 |
| 11 | 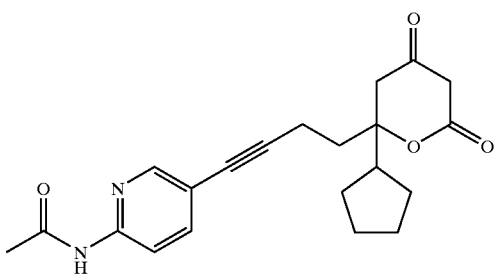 | 67 |

TABLE 1-continued

HCV Polymerase Inhibition Assay

| Example Number | Structure | IC$_{50}$ (μM) |
| --- | --- | --- |
| 12 | 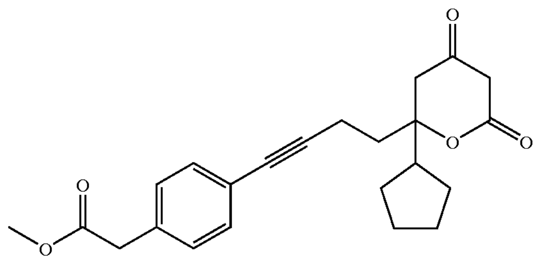 | 10.2 |
| 13 | 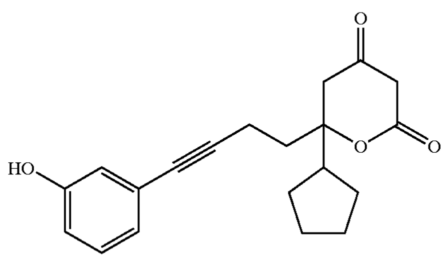 | 4.5 |
| 14 | 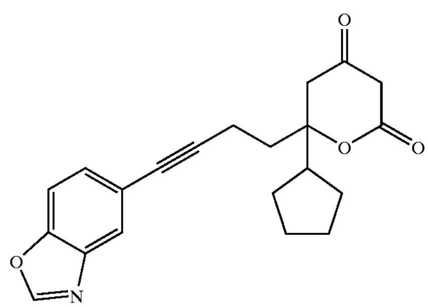 | 5.8 |
| 15 | 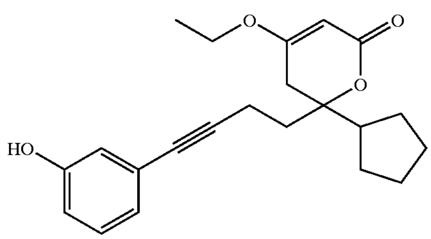 | 27% inhib @ 50 μM |
| 16 | 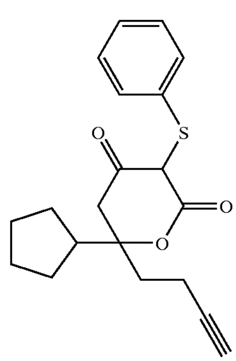 | 80.0 |

TABLE 1-continued

HCV Polymerase Inhibition Assay

| Example Number | Structure | IC$_{50}$ ($\mu$M) |
|---|---|---|
| 17 | 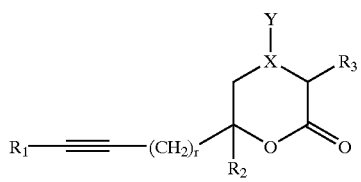 | 7.6 |

While the invention has been described in terms of various preferred embodiments and specific examples, the invention should be understood as not being limited by the foregoing detailed description, but as being defined by the appended claims and their equivalents.

What is claimed is:

1. A compound represented by formula (I):

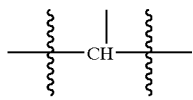
(I)

wherein:

r is 0, 1, 2, 3, 4 or 5;

Y is =O or —O(CH$_m$)$_n$, where m is 2 or 3 and n is an integer from 0 to 5;

X is

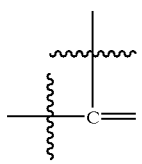

when Y is —O(CH$_m$)$_n$ and X is

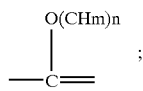

when Y is =O; or X and Y taken together $$\underset{-C=}{\overset{O(CHm)n}{|}}\ ;$$

R$_1$ is hydrogen, or an aryl, heteroaryl, or heterocycloalkyl group unsubstituted or substituted with one or more substituents selected from the group consisting of halogens; =O; =S; —CN; —NO$_2$; alkyl; heteroalkyl; alkenyl; alkynyl; aryl; cycloalkyl; heterocycloalkyl: heteroaryl; alkoxy; —(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHSH; —NHS(O)H; —NHSO$_2$H; —C(O)SH; —C(O)S(O)H; —C(O)S(O$_2$)H; —C(S)OH; —C(SO)OH; —C(SO$_2$)OH; —NHC(S)H; —OC(S)H; —OC(S)OH; —OC(SO$_2$)H; —S(O$_2$)NH$_2$; —S(O)NH$_2$; —SNH$_2$; —NHCS(O$_2$)H; —NHC(SO)H; —NHC(S)H; and —SH groups, unsubstituted or substituted with one or more substituents selected from the group consisting of halogens; =O; =S; —CN; —NO$_2$; alkyl; heteroalkyl; alkenyl; alkynyl; aryl; cycloalkyl; heterocycloalkyl; heteroaryl; alkoxy; —(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHSH; —NHS(O)H; —NHSO$_2$H; —C(O)SH; —C(O)S(O)H; —C(O)S(O$_2$)H; —C(S)H; —C(SO)OH; —C(SO$_2$)OH; —NHC(S)H; —OC(S)H; —OC(S)OH; —OC(SO$_2$)H; —S(O$_2$)NH$_2$; —S(O)NH$_2$;

—SNH$_2$; —NHCS(O$_2$)H; —NHC(SO)H; —NHC(S)H; and —SH groups; and

R$_2$ is a cyclopentyl group, unsubstituted or substituted with one or more substituents selected from the group consisting of halogens; =O; =S; —CN; —NO$_2$; alkyl; alkenyl; alkynyl; aryl; cycloalkyl; heterocycloalkyl; heteroaryl; —(CH$_2$)$_z$CN where z is an integer from 1 to 4; =NH; —NHOH; —OH; —C(O)H; —OC(O)H; —C(O)OH; —OC(O)OH; —OC(O)OC(O)H; —OOH; —C(NH)NH$_2$; —NHC(NH)NH$_2$; —C(S)NH$_2$; —NHC(S)NH$_2$; —NHC(O)NH$_2$; —S(O$_2$)H; —S(O)H; —NH$_2$; —C(O)NH$_2$; —OC(O)NH$_2$; —NHC(O)H; —NHC(O)OH; —C(O)NHC(O)H; —OS(O$_2$)H; —OS(O)H; —OSH; —SC(O)H; —S(O)C(O)OH; —SO$_2$C(O)OH; —NHSH; —NHS(O)H; —NHSO$_2$H; —C(O)SH; —C(O)S(O)H; —C(O)S(O$_2$)H; —C(S)OH; —C(SO)OH; —C(SO$_2$)OH; —NHC(S)H; —OC(S)H; —OC(S)OH; —OC(SO$_2$)H; —S(O$_2$)NH$_2$; —S(O)NH$_2$; —SNH$_2$; —NHCS(O$_2$)H; —NHC(SO)H; —NHC(S)H; and —SH groups; and R$_3$ is hydrogen, =S, or SH unsubstituted or substituted with an aryl group; or a pharmaceutically acceptable salt thereof.

2. A compound or pharmaceutically acceptable salt according to claim 1, wherein R$_2$ is an unsubstituted cyclopentyl group.

3. A compound or pharmaceutically acceptable salt according to claim 2, wherein R$_3$ is hydrogen.

4. A compound or pharmaceutically acceptable salt according to claim 3, wherein R$_1$ is a heteroaryl group or a phenyl group, unsubstituted or substituted with one or more substituents selected from the group consisting of halogens; =O; —OH; =S; —SH; —N; alkyl; alkenyl; alkynyl; and —CH(CH$_3$)$_2$; or two or more substituents cyclized to form a fused or spiro polycyclic cycloalkyl; heterocycloalkyl; aryl; or heteroaryl group.

5. A compound according to claim 4, wherein R$_1$ is a phenyl group or an unsubstituted heteroaryl group.

6. A compound according to claim 5, wherein R$_1$ is a 5 membered heteroaryl ring including from 1 to 3 heteroatoms selected from N and S.

7. A compound selected from the group consisting of:

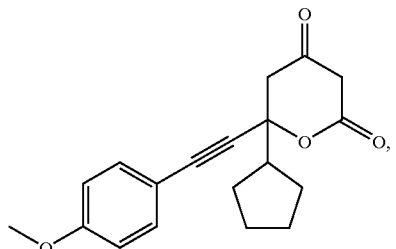

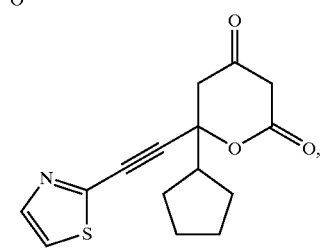

-continued

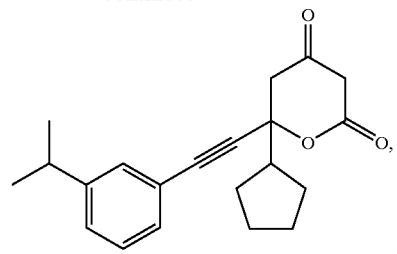

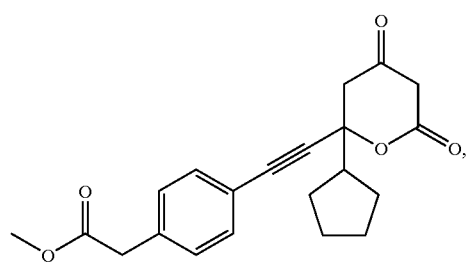

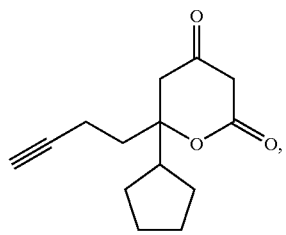

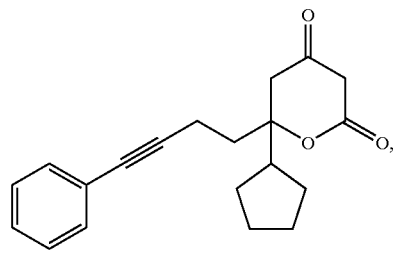

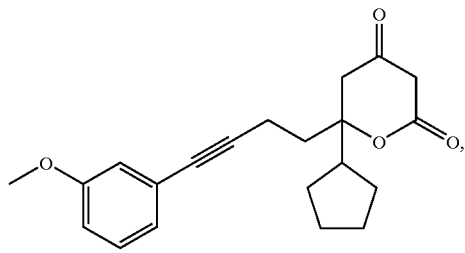

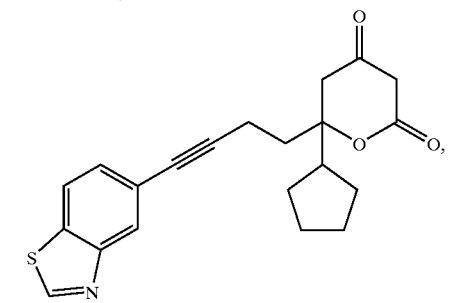

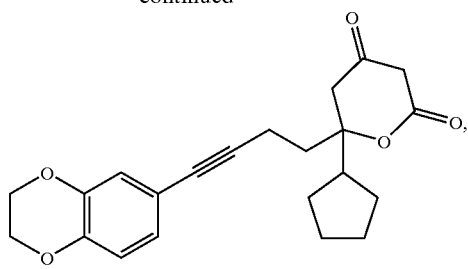
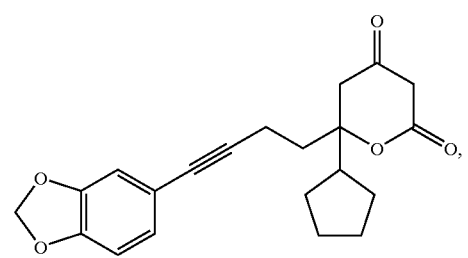
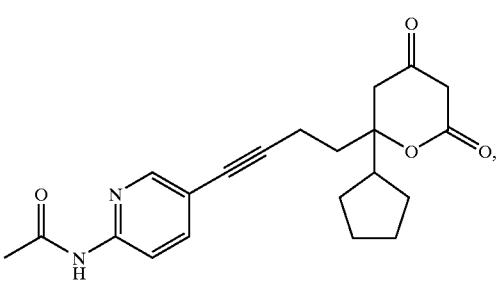
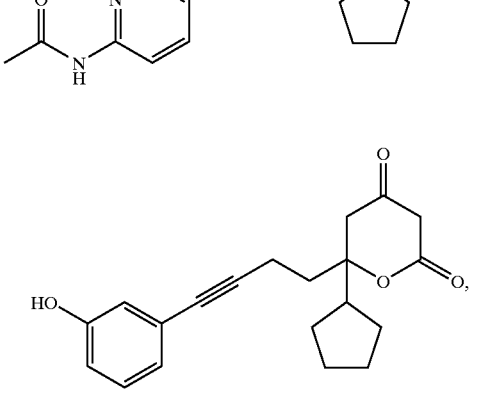
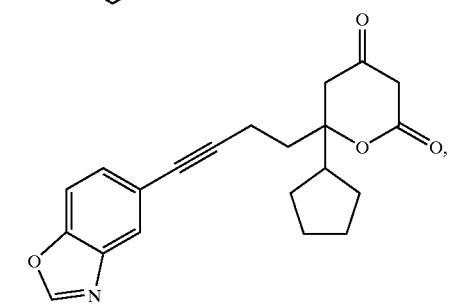
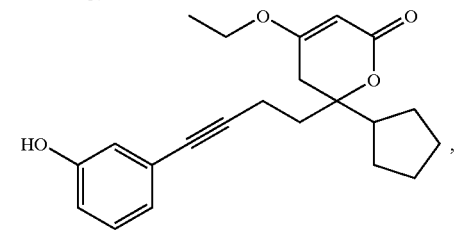
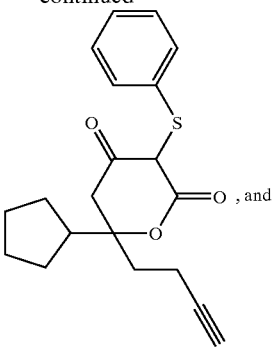
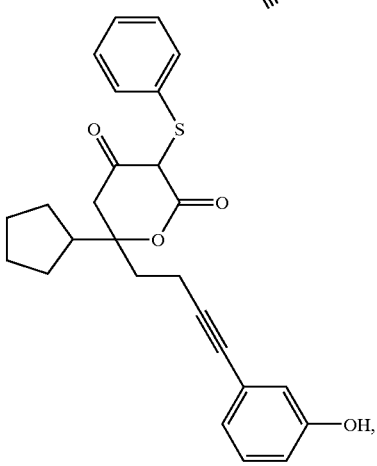
or a pharmaceutically acceptable salt thereof.
8. A compound represented by formula (I):
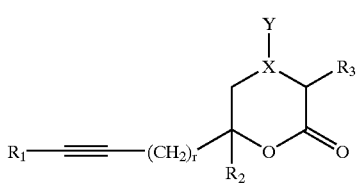
wherein:
r is 0, 1 or 2;
Y is =O or —O(CH$_m$)$_n$, where m is 2 or 3 and n is an integer from 0 to 5;
X is
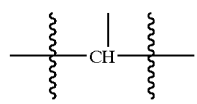
when Y is —O(CH$_m$)$_n$ and X is
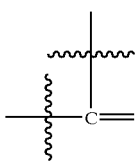

when Y is =O; or X and Y taken together form

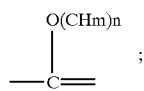

R$_1$ is hydrogen, or an aryl, or heteroaryl, unsubstituted or substituted with one or more substituents selected from the group consisting of alkyl; alkoxy; —OH; —NHC(O)H; and —SH groups, unsubstituted or substituted with one or more substituents selected from the group consisting of =O; alkyl; and alkoxy groups; and R$_2$ is a cyclopentyl group; and R$_3$ is hydrogen;

or a pharmaceutically acceptable salt thereof.

9. A pharmaceutical composition comprising: a therapeutically effective HCV-inhibiting amount of a compound or salt as defined in claim 1; and a pharmaceutically acceptable carrier.

* * * * *